United States Patent
Park et al.

(10) Patent No.: US 12,371,459 B2
(45) Date of Patent: Jul. 29, 2025

(54) ANTIMICROBIAL PEPTIDE DERIVED FROM PSEUDIN-2 PEPTIDE AND USES THEREOF

(71) Applicant: INDUSTRY-ACADEMIC COOPERATION FOUNDATION, CHOSUN UNIVERSITY, Gwangju (KR)

(72) Inventors: Yoonkyung Park, Jeollanam-do (KR); Hee Kyoung Kang, Gwangju (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 875 days.

(21) Appl. No.: 17/438,839

(22) PCT Filed: Oct. 14, 2019

(86) PCT No.: PCT/KR2019/013410
§ 371 (c)(1),
(2) Date: Sep. 13, 2021

(87) PCT Pub. No.: WO2020/197016
PCT Pub. Date: Oct. 1, 2020

(65) Prior Publication Data
US 2022/0153789 A1    May 19, 2022

(30) Foreign Application Priority Data
Mar. 25, 2019  (KR) .................. 10-2019-0033427

(51) Int. Cl.
| | | |
|---|---|---|
| *C07K 14/46* | (2006.01) | |
| *A01N 63/10* | (2020.01) | |
| *A23B 2/729* | (2025.01) | |
| *A23K 20/147* | (2016.01) | |
| *A23K 20/195* | (2016.01) | |
| *A23L 33/18* | (2016.01) | |
| *A61K 8/64* | (2006.01) | |
| *A61Q 17/00* | (2006.01) | |

(52) U.S. Cl.
CPC ............ *C07K 14/463* (2013.01); *A01N 63/10* (2020.01); *A23B 2/7295* (2025.01); *A23K 20/147* (2016.05); *A23K 20/195* (2016.05); *A23L 33/18* (2016.08); *A61K 8/64* (2013.01); *A61Q 17/005* (2013.01)

(58) Field of Classification Search
CPC .... C07K 14/463; A01N 63/10; A23K 20/195; A23L 3/34635; A23L 33/18; A61K 8/64; A61K 38/00; A61Q 17/005; A01P 1/00; A61P 31/04
See application file for complete search history.

(56) References Cited

FOREIGN PATENT DOCUMENTS

| KR | 10-2010-0042768 A | 4/2010 |
|---|---|---|
| KR | 10-1038542 B1 | 6/2011 |
| KR | 10-2017-0032689 A | 3/2017 |

OTHER PUBLICATIONS

International Search Report for PCT/KR2019/013410 mailed on Mar. 20, 2020.
Merrifield, RB et al. "Solid Phase Peptide Synthesis I. The Synthesis of a Tetrapeptide", J. Am. Chem. Soc., 85, 2149, 1963.
James A. Hill et al., "Matrix-assisted Laser Desorption Ionization with a Magnetic Mass Spectrometer", Rapid Communications in Mass Spectrometry, vol. 5, pp. 395-399, 1991.
NCBI, GenBank accession No. P83189.1, RecName: Full=Pseudin-2.
Loyd Olson III et al., "Pseudin-2: An Antimicrobial Peptide with Low Hemolytic Activity from the Skin of the Paradoxical Frog", Biochemical and Biophysical Research Communications, vol. 288, No. 4, pp. 1001-1005, 2001.
Seong-Cheol Park et al., "A plausible mode of action of pseudin-2, an antimicrobial peptide from Pseudis paradoxa", Biochimica et Biophysica Acta, 1808, pp. 171-182, 2011.

*Primary Examiner* — Lianko G Garyu
*Assistant Examiner* — Erinne R Dabkowski
(74) *Attorney, Agent, or Firm* — The PL Law Group, PLLC

(57) ABSTRACT

An antimicrobial peptide according to an embodiment of the present disclosure has the amino acid sequence of SEQ ID NO: 1, wherein i) the 1st and the 20th to the 24th amino acids are deleted, ii) the 1st and the 20th to the 24th amino acids are deleted and the 11th or the 18th amino acid is substituted with lysine (K), or iii) the 1st and the 20th to the 24th amino acids are deleted and the 11th and the 18th amino acids are substituted with lysine (K).

14 Claims, 8 Drawing Sheets
Specification includes a Sequence Listing.

SEQUENCE LISTING

```
<160> NUMBER OF SEQ ID NOS: 15

<210> SEQ ID NO 1
<211> LENGTH: 24
<212> TYPE: PRT
<213> ORGANISM: Artificial Sequence
<220> FEATURE:
<223> OTHER INFORMATION: Pseudin-2

<400> SEQUENCE: 1

Gly Leu Asn Ala Leu Lys Lys Val Phe Gln Gly Ile His Glu Ala Ile
1               5                   10                  15

Lys Leu Ile Asn Asn His Val Gln
            20

<210> SEQ ID NO 2
<211> LENGTH: 24
<212> TYPE: PRT
<213> ORGANISM: Artificial Sequence
<220> FEATURE:
<223> OTHER INFORMATION: Pse-11G-K

<400> SEQUENCE: 2

Gly Leu Asn Ala Leu Lys Lys Val Phe Gln Lys Ile His Glu Ala Ile
1               5                   10                  15

Lys Leu Ile Asn Asn His Val Gln
            20

<210> SEQ ID NO 3
<211> LENGTH: 24
<212> TYPE: PRT
<213> ORGANISM: Artificial Sequence
<220> FEATURE:
<223> OTHER INFORMATION: Pse-18L-K

<400> SEQUENCE: 3

Gly Leu Asn Ala Leu Lys Lys Val Phe Gln Gly Ile His Glu Ala Ile
1               5                   10                  15

Lys Lys Ile Asn Asn His Val Gln
            20

<210> SEQ ID NO 4
<211> LENGTH: 24
<212> TYPE: PRT
<213> ORGANISM: Artificial Sequence
<220> FEATURE:
<223> OTHER INFORMATION: Pse-11G/18L-K
```

```
<400> SEQUENCE: 4

Gly Leu Asn Ala Leu Lys Lys Val Phe Gln Lys Ile His Glu Ala Ile
1               5                   10                  15

Lys Lys Ile Asn Asn His Val Gln
            20

<210> SEQ ID NO 5
<211> LENGTH: 24
<212> TYPE: PRT
<213> ORGANISM: Artificial Sequence
<220> FEATURE:
<223> OTHER INFORMATION: Pse-Anal1

<400> SEQUENCE: 5

Trp Leu Asn Ala Leu Lys Lys Val Phe Gln Gly Ile His Glu Ala Ile
1               5                   10                  15

Lys Leu Ile Asn Asn His Val Gln
            20

<210> SEQ ID NO 6
<211> LENGTH: 24
<212> TYPE: PRT
<213> ORGANISM: Artificial Sequence
<220> FEATURE:
<223> OTHER INFORMATION: Pse-Anal2

<400> SEQUENCE: 6

Trp Leu Asn Ala Leu Lys Lys Val Phe Gln Gly Ile His Glu Ala Ile
1               5                   10                  15

Lys Leu Ile Trp Asn His Val Gln
            20

<210> SEQ ID NO 7
<211> LENGTH: 24
<212> TYPE: PRT
<213> ORGANISM: Artificial Sequence
<220> FEATURE:
<223> OTHER INFORMATION: Pse-Anal3

<400> SEQUENCE: 7

Trp Leu Asn Ala Leu Lys Lys Val Phe Gln Gly Ile His Glu Ala Ile
1               5                   10                  15

Lys Leu Ile Trp Asn Trp Val Gln
            20

<210> SEQ ID NO 8
<211> LENGTH: 24
<212> TYPE: PRT
<213> ORGANISM: Artificial Sequence
<220> FEATURE:
<223> OTHER INFORMATION: Pse-Anal4

<400> SEQUENCE: 8

Trp Leu Asn Ala Leu Lys Lys Val Trp Gln Gly Ile His Glu Ala Ile
1               5                   10                  15

Lys Leu Ile Trp Asn Trp Val Gln
            20

<210> SEQ ID NO 9
<211> LENGTH: 24
<212> TYPE: PRT
<213> ORGANISM: Artificial Sequence
<220> FEATURE:
```

```
<223> OTHER INFORMATION: Pse-Ana15

<400> SEQUENCE: 9

Gly Leu Asn Ala Leu Lys Lys Val Ser Gln Gly Ile His Glu Ala Ile
1               5                   10                  15

Lys Leu Ile Asn Asn His Val Gln
            20

<210> SEQ ID NO 10
<211> LENGTH: 24
<212> TYPE: PRT
<213> ORGANISM: Artificial Sequence
<220> FEATURE:
<223> OTHER INFORMATION: Pse-Ana16

<400> SEQUENCE: 10

Gly Leu Asn Ala Leu Lys Lys Val Ser Gln Gly Ile His Glu Ser Ile
1               5                   10                  15

Lys Leu Ile Asn Asn His Val Gln
            20

<210> SEQ ID NO 11
<211> LENGTH: 24
<212> TYPE: PRT
<213> ORGANISM: Artificial Sequence
<220> FEATURE:
<223> OTHER INFORMATION: Pse-Ana17

<400> SEQUENCE: 11

Ala Leu Asn Ala Leu Lys Lys Val Ser Gln Gly Ile His Glu Ala Ile
1               5                   10                  15

Lys Leu Ile Ala Asn His Val Gln
            20

<210> SEQ ID NO 12
<211> LENGTH: 18
<212> TYPE: PRT
<213> ORGANISM: Artificial Sequence
<220> FEATURE:
<223> OTHER INFORMATION: Pse-T1

<400> SEQUENCE: 12

Leu Asn Ala Leu Lys Lys Val Phe Gln Gly Ile His Glu Ala Ile Lys
1               5                   10                  15

Leu Ile

<210> SEQ ID NO 13
<211> LENGTH: 18
<212> TYPE: PRT
<213> ORGANISM: Artificial Sequence
<220> FEATURE:
<223> OTHER INFORMATION: Pse-T2

<400> SEQUENCE: 13

Leu Asn Ala Leu Lys Lys Val Phe Gln Lys Ile His Glu Ala Ile Lys
1               5                   10                  15

Leu Ile

<210> SEQ ID NO 14
<211> LENGTH: 18
<212> TYPE: PRT
<213> ORGANISM: Artificial Sequence
<220> FEATURE:
<223> OTHER INFORMATION: Pse-T3
```

```
<400> SEQUENCE: 14

Leu Asn Ala Leu Lys Lys Val Phe Gln Gly Ile His Glu Ala Ile Lys
1               5                   10                  15

Lys Ile

<210> SEQ ID NO 15
<211> LENGTH: 18
<212> TYPE: PRT
<213> ORGANISM: Artificial Sequence
<220> FEATURE:
<223> OTHER INFORMATION: Pse-T4

<400> SEQUENCE: 15

Leu Asn Ala Leu Lys Lys Val Phe Gln Lys Ile His Glu Ala Ile Lys
1               5                   10                  15

Lys Ile
```

US 12,371,459 B2

ANTIMICROBIAL PEPTIDE DERIVED FROM PSEUDIN-2 PEPTIDE AND USES THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/013410, filed Oct. 14, 2019, which claims priority to the benefit of Korean Patent Application No. 10-2019-0033427 filed in the Korean Intellectual Property Office on Mar. 25, 2019, the entire contents of which are incorporated herein by reference.

BACKGROUND

1. Technical Field

The present invention relates to a novel antimicrobial peptide derived from Pseudin-2 peptide and uses thereof.

2. Background Art

Bacterial infection is one of the most common and deadly causes of a human disease. Unfortunately, due to abuse of antibiotics, bacterial resistance to antibiotics has been yielded. The rate of exhibiting resistance to antibiotics by bacteria is indeed much faster than the rate of developing new analogs of the antibiotics. For example, various bacterial species like *Enterococcus faecalis, Acinetobacter baumannii*, and *Pseudomonas aeruginosa*, which may pose a threat to human life, have developed resistance to all antibiotics that are known until now.

Antibiotic tolerance is a phenomenon that is distinguished from the resistance to antibiotics, and after being found first in *Pneumococcus* sp. in 1970s, it provides an important clue for studying the working mechanism of penicillin. Bacterial species exhibiting the tolerance show growth stall in the presence of antibiotics at common concentration, but without any death. The tolerance is caused due to a lack of the activity of an autolytic bacterial enzyme like autolysin as the antibiotics inhibit an enzyme for synthesizing cell wall, and this leads to the results that, as an endogenous hydrolytic enzyme is activated by penicillin, bacterial cell death is caused, and the bacteria also suppress the enzyme activity to survive even under a treatment with antibiotics.

Having bacterial tolerance to various antibiotics is clinically very important because, once it becomes impossible to eradicate bacteria with tolerance, usefulness of a clinical treatment with antibiotics for infection is impaired. Furthermore, having tolerance is believed to be a prerequisite requirement for developing resistance to antibiotics, and that is because there are bacterial strains which manage to survive even after a treatment with antibiotics. By acquiring new genetic elements to exhibit resistance to antibiotics, those bacterial strains keep growing even in the presence of the antibiotics. Since all bacteria exhibiting resistance are indeed known to have tolerance too, it is necessary to develop novel antibiotics which can be used for eradicating those bacteria having resistance to antibiotics.

In terms of working mechanism, the tolerance to antibiotics broadly consists of two pathways. The first pathway is phenotypic tolerance which occurs during every bacteria growth with decreasing rate, and the second pathway is genetic tolerance caused by mutation which occurs in specific types of bacteria. In all of those cases, the basic phenomenon is an occurrence of down regulation of autolysin activity. This down regulation is transient in case of phenotypic tolerance against external stimulation, while it is permanent in case of genetic tolerance in which a mutation for causing a change in pathway for regulating cell lysis occurs. The simplest genetic tolerance is based on a defect in autolysin enzyme, and due to various kinds of reasons which have not been clarified, a bacterial strain having the tolerance as caused by a defect in suicidal enzyme has not been clinically found yet, and clinical tolerance is rather achieved via regulation of the activity of autolysin.

As discussed in the above, in order to deal with bacteria which exhibit resistance to antibiotics, development of new antibiotics is necessary, and also development of new antibiotics which function independently of the activity of autolysin is required.

Meanwhile, by synthesizing peptides or small organic molecules, bacteria may kill neighboring bacteria, and, in terms of the structure, those bacteriocins are categorized into three classes. First class is lantibiotics, second class is nonlantibiotics, and third class is those secreted by signal peptides. Animals including insects also produce peptide antibiotics that are naturally produced, and those antibiotics are categorized into three groups based on their structure. First group is cysteine-rich β-sheet peptides, second group is α-helical amphipathic molecules, and third group is proline-rich peptides. Those antimicrobial peptides are known to play an important role in host defense and innate immune system and they have various structures depending on their amino acid sequence.

Meanwhile, in Korean Patent Publication No. 2010-0042768, "Biodegradable polymer microsphere for sustained and controlled release of Pseudin-2 or homologs thereof and production method thereof" is disclosed, and, in Korean Patent Registration No. 1038542, "Novel antimicrobial peptide homolog derived from Pseudin having high bacterial selectivity by substitution with lysine and proline residues and its use" is disclosed. However, the novel antimicrobial peptide derived from Pseudin-2 consisting of the amino acid sequence of SEQ ID NO: 12 to 15 and uses thereof as described in the present invention have never been disclosed before.

SUMMARY

The present invention is devised under the circumstances described above. Specifically, by using as a template the amphiphilic Pseudin-2 antimicrobial peptide which has been previously reported to have an antimicrobial activity, the inventors of the present invention synthesized 14 novel types of Pseudin-2 homologs (SEQ ID NO: 2 to SEQ ID NO: 15) having enhanced antimicrobial activity, and among the aforementioned peptide homologs which have been synthesized, Pse-T1, Pse-T2, Pse-T3 and Pse-T4 peptides (SEQ ID NO: 12 to SEQ ID NO: 15) have better antimicrobial activity for Gram-positive bacteria, Gram-negative bacteria, yeast, and antimicrobial tolerant bacteria and exhibit lower cytotoxicity for mouse erythrocytes and a normal human cell line when compared to Pseudin-2 as a mother peptide. The present invention is completed accordingly.

In order to solve the problems described above, the present invention provides an antimicrobial peptide in which, in the amino acid sequence of SEQ ID NO: 1, i) the $1^{st}$ and the $20^{th}$ to the $24^{th}$ amino acids are deleted, ii) the $1^{st}$ and the $20^{th}$ to the $24^{th}$ amino acids are deleted and the $11^{th}$ or the $18^{th}$ amino acid is substituted with lysine (K), or iii)

the 1st and the 20th to the 24th amino acids are deleted and the 11th and the 18th amino acids are substituted with lysine(K).

The present invention further provides antibiotics comprising the aforementioned antimicrobial peptide as an effective component.

The present invention further provides an antimicrobial cosmetic composition comprising the aforementioned antimicrobial peptide as an effective component.

The present invention further provides an antimicrobial food additive comprising the aforementioned antimicrobial peptide as an effective component.

The present invention further provides an antimicrobial animal feed additive comprising the aforementioned antimicrobial peptide as an effective component.

The present invention further provides antimicrobial biopesticides comprising the aforementioned antimicrobial peptide as an effective component.

The present invention further provides an antimicrobial quasi-drug composition comprising the aforementioned antimicrobial peptide as an effective component.

The present invention still further provides a method for antimicrobial treatment in a subject including administering a pharmaceutically effective amount of the aforementioned antimicrobial peptide to the subject.

Among the Pseudin-2 homolog antimicrobial peptides of the present invention, the peptides of the present invention (Pse-T1, Pse-T2, Pse-T3 and Pse-T4) which have a deletion and/or a substitution of amino acids have not only an excellent antimicrobial activity but also low cytotoxicity, and therefore they can be advantageously used as an effective component of antibiotics, cosmetic composition, food additive, animal feed additive, biopesticides, quasi-drug, and the like.

DETAILED DESCRIPTION

Figure 1:
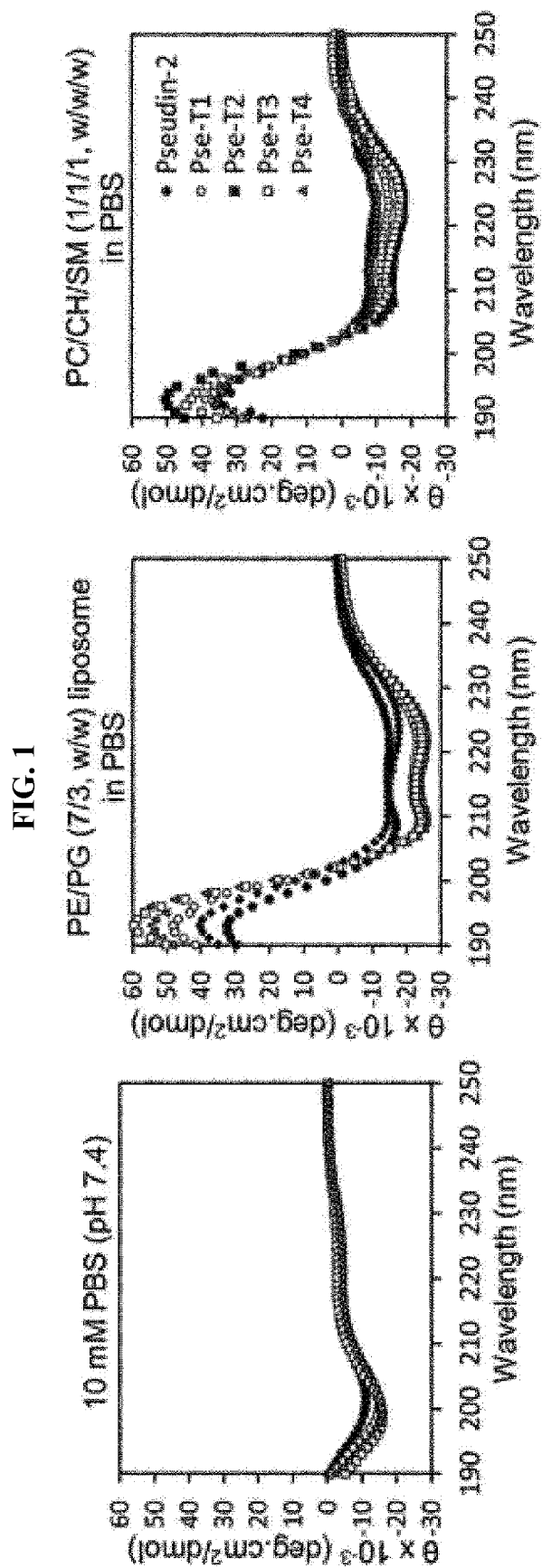
FIG. 1 illustrates the result of determining, in membrane-like environment, the secondary structure of Pseudin-2 (control) as an antimicrobial peptide and Pse-T1, Pse-T2, Pse-T3 and Pse-T4 (test group), which are novel Pseudin-2 homolog peptides in which the C-terminus has been deleted and several amino acids have been substituted. Specifically, drawing on the left represents the structure in aqueous state (10 mM PBS solution), drawing at the center represents the structure in artificial membrane composed of PE/PG (7/3), which mimics bacteria membrane, and drawing on the right represents the structure in artificial membrane composed of PC/CH/SM (1/1/1), which mimics the membrane of a eukaryotic cell.
Figure 2:
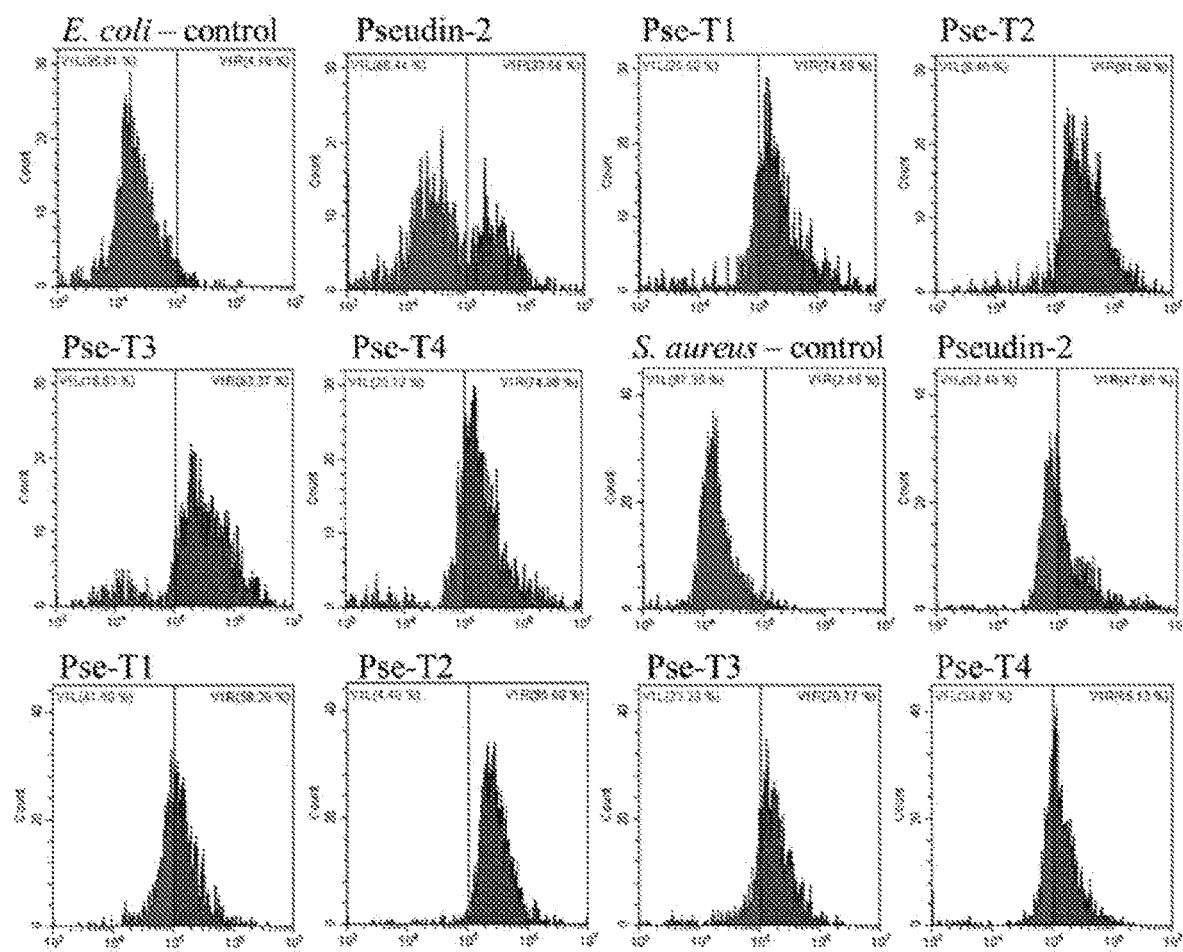
FIG. 2 illustrates the result of determining the action of Pseudin-2 peptide as a control and novel peptides Pse-T1, Pse-T2, Pse-T3 and Pse-T4 on the membrane of *Escherichia coli* and *Staphylococcus aureus*, in which the determination was made by flow cytometry (FACS).

To achieve the purpose of the present invention, the present invention provides an antimicrobial peptide in which, in the amino acid sequence of SEQ ID NO: 1, i) the 1st and the 20th to the 24th amino acids are deleted, ii) the 1st and the 20th to the 24th amino acids are deleted and the 11th or the 18th amino acid is substituted with lysine, or iii) the 1st and the 20th to the 24th amino acids are deleted and the 11th and the 18th amino acids are substituted with lysine.

Pseudin-2 peptide as a mother peptide previously known to have the amino acid sequence of SEQ ID NO: 1 is an antimicrobial peptide derived from a paradox frog (*Pseudis paradoxa*), and it is known to be an antimicrobial peptide. Pseudin-2 peptide can be produced by a method for synthesizing peptide that is well known in the pertinent art, and the production method is not particularly limited. As for the method for synthesis, synthesis is preferably carried out according to a method for chemical synthesis of a peptide which is commonly employed in the pertinent art. More preferably, synthesis is carried out by a solution phase peptide synthesis, a solid-phase peptide synthesis, a fragment condensation method, or F-moc or T-BOC chemical method. Most preferably, synthesis is carried out by a solution phase peptide synthesis (Merrifield, R B., J. Am. Chem. Soc., 85, 2149, 1963), but it is not limited thereto.

The antimicrobial peptide of the present invention needs to satisfy the requirement i), ii), or iii) that are described above. Specifically, the requirement i) is that the 1st and the 20th to the 24th amino acids of the mother peptide of SEQ ID NO: 1 are all deleted, the requirement ii) is that the 1st and the 20th to the 24th amino acids of the mother peptide of SEQ ID NO: 1 are all deleted and glycine (G) as the 11th amino acid or leucine (L) as the 18th amino acid of the mother peptide of SEQ ID NO: 1 is substituted with lysine (K), which is a basic amino acid with positive charge, and the requirement iii) is that the 1st and the 20th to the 24th amino acids of the mother peptide of SEQ ID NO: 1 are all deleted and glycine (G) as the 11th amino acid and leucine (L) as the 18th amino acid of the mother peptide of SEQ ID NO: 1 are substituted with lysine (K).

The antimicrobial peptide of the present invention may preferably have the amino acid sequence of SEQ ID NO: 12 to 15. Peptide having the amino acid sequence of SEQ ID NO: 12 is an antimicrobial peptide in which the 1st and the 20th to the 24th amino acids are all deleted from Pseudin-2 as a mother peptide, and the peptide is named Pse-T1. Peptide having the amino acid sequence of SEQ ID NO: 13 is an antimicrobial peptide in which the 1st and the 20th to the 24th amino acids are all deleted from Pseudin-2 as a mother peptide and glycine as the 11$^{th}$ amino acid is substituted with lysine, and the peptide is named Pse-T2. Peptide having the amino acid sequence of SEQ ID NO: 14 is an antimicrobial peptide in which the 1$^{st}$ and the 20$^{th}$ to the 24$^{th}$ amino acids are all deleted from Pseudin-2 as a mother peptide and leucine as the 18$^{th}$ amino acid is substituted with lysine, and the peptide is named Pse-T3. Peptide having the amino acid sequence of SEQ ID NO: 15 is an antimicrobial peptide in which the 1$^{st}$ and the 20$^{th}$ to the 24$^{th}$ amino acids are all deleted from Pseudin-2 as a mother peptide and glycine as the 11$^{th}$ amino acid and leucine as the 18$^{th}$ amino acid are substituted with lysine, and the peptide is named Pse-T4. According to utilization of increase/decrease of electric charge, the substitution can lower the cytotoxicity and the substitution may be carried out to enhance or maintain the antimicrobial activity against Gram-negative bacteria, Gram-positive bacteria, yeast, or bacteria having tolerance to antibiotics.

It is preferable that the antimicrobial peptide of the present invention has an antimicrobial activity against Gram-positive bacteria, Gram-negative bacteria, yeast, or bacteria having tolerance to antibiotics, but it is not limited thereto.

Gram-negative bacteria are preferably any Gram-negative bacteria that are known in the pertinent art including Gram-negative bacteria of genus *Pseudomonas*, genus *Escherichia*, genus *Salmonella*, genus *Leptospira*, and genus *Rickettsia*. Gram-negative bacteria are more preferably bacteria of genus *Pseudomonas*, genus *Salmonella*, or genus *Escherichia*. Gram-negative bacteria are most preferably *Escherichia coli, Pseudomonas aeruginosa*, or *Salmonella typhimurium*, but they are not limited thereto.

Gram-positive bacteria are preferably any Gram-positive bacteria that are known in the pertinent art including Gram-positive bacteria of genus *Staphylococcus*, genus *Listeria*, genus *Corynebacterium*, genus *Lactobacillus*, and genus *Bacillus*. Gram-positive bacteria are more preferably Gram-positive bacteria of genus *Staphylococcus*, genus *Bacillus*, or genus *Listeria*. Gram-positive bacteria are most preferably *Staphylococcus aureus, Bacillus subtilis*, or *Listeria monocytogenes*, but they are not limited thereto.

Yeast is preferably the yeast of genus *Candida* or genus *Trichosporon*, and most preferably *Candida albicans* or *Trichosporon beigelii*, but it is not limited thereto.

The bacteria having tolerance to antibiotics is preferably one or more selected from a group consisting of *Pseudomonas aeruginosa, Escherichia coli*, and *Staphylococcus aureus* which have tolerance to antibiotics, but they are not limited thereto.

Examples of the antibiotics include, although not limited thereto, aminoglycoside-based (aminoglycoside, gentamycin, neomycin, and the like), penicillin-based (ampicillin and the like), sulfonamide-based, beat-lactam based (beta-lactam, amoxicillin/clavulanic acid, and the like), chloramphenicol-based, erythromycin-based, florfenicol-based, fosfmycin-based, kanamycin-based, lincomycin-based, meticillin-based, quinolone-based, streptomycin-based, tetracycline-based, trimethoprim-based, and vancomycin-based antibiotics.

The antimicrobial peptide of the present invention may be a peptide which exhibits low cytotoxicity for cells derived from human, but it is not limited thereto.

The present invention further provides antibiotics comprising the aforementioned antimicrobial peptide as an effective component. The antimicrobial peptide is preferably a peptide having an amino acid sequence selected from a group of the amino acids of SEQ ID NO: 12 to SEQ ID NO: 15, and the peptide is the same as described in the above.

Since Pse-T1 (SEQ ID NO: 12), Pse-T2 (SEQ ID NO: 13), Pse-T3 (SEQ ID NO: 14) and Pse-T4 (SEQ ID NO: 15) of the present invention, which are a homolog antimicrobial peptide derived from Pseudin-2 antimicrobial peptide, exhibit low cytotoxicity for cells derived from human while having a strong antimicrobial activity against Gram-positive bacteria, Gram-negative bacteria, yeast, and bacteria having tolerance to antibiotics, the antimicrobial peptide of the present invention can be advantageously used as an effective component of antibacterial antibiotics.

For clinical administration, the peptide of the present invention can be administered parenterally, and it can be used in the form of a common pharmaceutical preparation. Parenteral administration may mean administration via a route other than oral administration like rectal, intravenous, intraperitoneal, intramuscular, intraarterial, transdermal, nasal, inhalational, intraocular, and subcutaneous administration. When the antimicrobial peptide of the present invention is used as a pharmaceutical product, one or more effective components exhibiting the same or similar activity may be additionally included.

Namely, the antimicrobial peptide of the present invention can be indeed administered as various parenteral preparations, and, in case of having a preparation, production is made by using a diluent or a vehicle such as filler, bulking agent, binding agent, moisturizing agent, disintegrating agent, or surfactant that are commonly used for producing a preparation. In a preparation for parenteral administration, a sterilized aqueous solution, a non-soluble preparation, a suspension, an oil preparation, a freeze-dried preparation, and a suppository are included. As a water insoluble solvent or a suspending solvent, propylene glycol, polyethylene glycol, or vegetable oil such as olive oil, and injectable ester such as ethylolate can be used. As a base for a suppository, witepsol, macrogol, tween 61, cacao fat, laurin fat, glycerogelatin, or the like can be used.

Furthermore, the antimicrobial peptide of the present invention can be used after being admixed with various pharmaceutically acceptable carriers such as physiological saline or organic solvent. To enhance the stability or absorption property, carbohydrates such as glucose, sucrose, or dextran, antioxidants such as ascorbic acid or glutathione, chelating agents, low molecular weight proteins, or other stabilizers can be used as a pharmaceutical agent.

Effective dose of the antimicrobial peptide of the present invention is 0.1 to 2 mg/kg, and preferably 0.5 to 1 mg/kg. Administration can be made 1 to 3 times a day.

Total effective amount of the novel peptide of the present invention in the antibiotics of the present invention can be administered to a patient as a single dose in bolus form or infusion during a relatively short period of time, and it can be also administered according to a fractionated treatment protocol by which multiple dose is administered for a long period of time. With regard to the concentration described above, the effective dose is determined by considering not only the pharmaceutical administration route and number of treatment but also other various factors including age, health state, or the like of a patient. Thus, by considering them, a person having common knowledge in the pertinent art may determine suitable effective dose depending on specific use of the novel peptide of the present invention as antibiotics.

The present invention further provides an antimicrobial cosmetic composition comprising the aforementioned antimicrobial peptide as an effective component.

The antimicrobial peptide is preferably a peptide having the amino acid sequence of SEQ ID NO: 12 to SEQ ID NO: 15, and it is the same as described above. This peptide exhibits low cytotoxicity for cells derived from human while showing a strong antimicrobial activity. As such, the antimicrobial peptide of the present invention can be advantageously used as an effective component of an antimicrobial cosmetic composition.

In the cosmetic composition of the present invention, components commonly used for a cosmetic composition are included in addition to the antimicrobial peptide, and examples thereof include a common auxiliary agent such as an antioxidant, a stabilizing agent, a solubilizing agent, vitamin, a pigment, or a fragrance, and a carrier.

In the cosmetic composition of the present invention, the peptide of the present invention may be added in an amount of 0.1 to 50% by weight, and preferably 1 to 10% by weight to the cosmetic composition.

The cosmetic composition of the present invention may be produced in any formulation that is produced commonly in the pertinent art. For example, it can be produced as a formulation such as a solution, a suspension, an emulsion, paste, gel, cream, lotion, powder, a soap, a surfactant-containing cleanser, oil, powder foundation, emulsion foundation, wax foundation, or spray, but it is not limited thereto. More specifically, it can be produced as a formulation such as softening cosmetic water (skin water), nutritive cosmetic water (milk lotion), nutritive cream, massage cream, essence, eye cream, cleansing cream, cleansing foam, cleansing water, pack, spray, or powder.

When the formulation of the present invention is paste, cream, or gel, animal oil, vegetable oil, wax, paraffin, starch, tragacanth, cellulose derivatives, polyethylene glycol, silicone, bentonite, silica, talc, or zinc oxide can be used as a carrier component.

When the formulation of the present invention is powder or spray, lactose, talc, silica, aluminum hydroxide, calcium silicate, or polyamide powder can be used as a carrier component. When the formulation is spray, in particular, a propellant such as chlorofluorohydrocarbon, propane/butane, or dimethyl ether may be additionally included.

When the formulation of the present invention is a solution or an emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

When the formulation of the present invention is a suspension, a liquid diluent such as water, ethanol, or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

When the formulation of the present invention is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamine, vegetable oil, lanolin derivatives, or ethoxylated glycerol fatty acid ester can be used as a carrier component.

The present invention further provides an antimicrobial food additive comprising the aforementioned antimicrobial peptide as an effective component.

The antimicrobial peptide is preferably a peptide having one or more amino acids sequences selected from a group consisting of the amino acid sequences of SEQ ID NO: 12 to SEQ ID NO: 15. This peptide exhibits low cytotoxicity for cells derived from human while showing a strong antimicrobial activity. As such, the antimicrobial peptide of the present invention can be advantageously used as an effective component of a food additive.

When the peptide of the present invention is used as a food additive, the peptide may be directly added or used with other food components, and it can be suitably used according to a general method. Blending amount of the effective component can be suitably determined depending on the purpose of use. In general, the peptide of the present invention is added in an amount of 15 parts by weight or less, and preferably 10 parts by weight or less relative to peptide raw materials. However, in case of application for a long period of time, the blending amount may be lower than the aforementioned range. As there is no problem in terms of the stability, the effective component may be used in an amount that is higher than the aforementioned range.

Type of the food is not particularly limited. Examples of the food to which the additive can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all foods in general sense are included therein.

The present invention further provides an antimicrobial animal feed additive comprising the aforementioned antimicrobial peptide as an effective component.

The antimicrobial peptide is preferably a peptide having one or more amino acids sequences selected from a group consisting of the amino acid sequences of SEQ ID NO: 12 to SEQ ID NO: 15, and it is the same as described above. This peptide exhibits low cytotoxicity for cells derived from human while showing a strong antimicrobial activity. As such, the antimicrobial peptide of the present invention can be advantageously used as an effective component of an animal feed additive.

The animal feed composition of the present invention has an effect of replacing existing antibiotics, inhibiting the growth of harmful pathogenic food bacteria to improve the health state of an animal, enhancing the body weight and meat quality of livestock, and enhancing the milk production amount and immunity of livestock. The animal feed composition of the present invention can be produced in the form of fermented animal feed, complete animal feed, pellets, silage, or the like.

The fermented animal feed can be produced by adding various microbes or enzymes other than the peptide of the present invention to ferment organic matters, and the complete animal feed can be produced by admixing the peptide of the present invention with various kinds of common animal feed. Animal feed in pellet form can be produced by applying heat and pressure to a complete feed in a pelletizing machine, and silage can be produced by fermenting forage with the microbes of the present invention. Fermented wet animal feed can be produced by, after collecting and transporting organic matters and admixing them with a vehicle at a certain ratio for moisture control and sterilization, fermenting organic matters like food waste at a temperature suitable for fermentation for 24 hours or longer to adjust moisture content to about 70%. Fermented dry animal feed can be produced according to adjustment of the moisture content to 30% to 40% or so by providing fermented wet animal feed additionally to a drying process.

The present invention further provides a preservative composition, antimicrobial biopesticides, and an antimicrobial quasi-drug composition comprising the aforementioned antimicrobial peptide as an effective component.

The antimicrobial peptide is preferably a peptide having one or more amino acids sequences selected from a group consisting of the amino acid sequences of SEQ ID NO: 12 to SEQ ID NO: 15, and it is the same as described above. This peptide exhibits low cytotoxicity for cells derived from human while showing a strong antimicrobial activity against Gram-positive bacteria, Gram-negative bacteria, yeast, and bacteria having tolerance to antibiotics. As such, the antimicrobial peptide of the present invention can be advantageously used as an effective component of antimicrobial biopesticides, a preservative composition, or an antimicrobial quasi-drug composition.

Examples of the preservative composition include a cosmetics preservative and a pharmaceutical preservative. The preservative agent for food, cosmetics preservative, and pharmaceutical preservative are an additive which is used to prevent deterioration, degradation, discoloration, and chemical change of those products, and examples thereof include a sterilizer and an antioxidant. Also included are functional antibiotics having an activity of inhibiting growth or sterilizing degrading bacteria in food product and pharmaceutical product according to suppression of proliferation of microbes like bacteria, fungi, and yeast. As an ideal condition required for such preservative composition, the composition should not have any toxicity and should exhibit the effect even with a trace amount.

When the composition of the present invention is used as a quasi-drug additive, the antimicrobial peptide may be directly added or used with other quasi-drug or quasi-drug components, and it can be suitably used according to a general method. Blending amount of the effective component can be suitably determined depending on the purpose of use.

The quasi-drug composition of the present invention is preferably a sterilizing cleanser, a shower foam, a mouth wash, a water tissue, a liquid soap, a hand wash, a humidifier filler, a mask, an ointment, a patch, or a filter filler, although it is not limited thereto.

The present invention further provides a method for antimicrobial treatment in a subject including administering a pharmaceutically effective amount of the aforementioned antimicrobial peptide to the subject. The subject may be a mammal excluding human, but it is not limited thereto.

Hereinbelow, the present invention is explained in greater detail in view of the Examples. However, it is evident that the following Examples are given only for exemplification of the present invention and by no means the present invention is limited to the following Examples.

EXAMPLES

Example 1. Synthesis, Isolation, and Purification of Peptide

According to the solution phase peptide synthesis by Merrifield (Merrifield, R B., J. Am. Chem. Soc., 85, 2149, 1963), the inventors of the present invention synthesized a novel antimicrobial peptide by substituting, in the amino acid sequence of Pseudin-2 as a mother peptide described with the amino acid sequence of SEQ ID NO: 1, just one or both of the $11^{th}$ and $18^{th}$ amino acid residues with lysine (K), substituting just one or 2, 3, or 4 of the $1^{st}$, $9^{th}$, $20^{th}$ and $22^{nd}$ amino acid residues with tryptophan (W), substituting just one or both of the $9^{th}$ and $15^{th}$ amino acid residues with serine (S), substituting the $1^{st}$ and $20^{th}$ amino acid residues with alanine (A), or substituting the $9^{th}$ amino acid residue with serine (S). In addition, to synthesize a novel peptide with deleted amino acids, peptide synthesis was carried out by deleing the $1^{st}$ and the $20^{th}$ to the $24^{th}$ amino acids from the sequence of Pseudin-2, Pse-11G-K, Pse-18L-K, and Pse-11G/18L-K (Table 1), respectively.

Specifically, for the peptide in which the peptide designed in the present invention has a carboxy terminal in $NH_2$ form, a rink amide MBHA-resin was used as a starting material, and, for the peptide having a carboxy terminal in OH form, a Fmoc (9-fluorenylmethoxycarbonyl)-amino acid-Wang resin was used as a starting material.

Peptide chain extension based on Fmoc-amino acid coupling was carried out by DCC (N-hydroxybenzotrizole (HOBt)-dicyclo-hexycarbodiimide) method. After coupling Fmoc-amino acid at the terminal amino acid of each peptide, the Fmoc group is removed by using NMP (20% piperidine/N-methyl pyrrolidone) solution. Then, after washing several times with NMP and DCM (dichloromethane), drying with nitrogen gas was carried out. Then, a solution in which TFA (trifluoroacetic acid), phenol, thioanisole, $H_2O$, and triisopropylsilane are mixed at ratio of 85:5:5:2.5:2.5 (v/v) was added thereto followed by reaction for 2 to 3 hours to remove the protective group and separate the peptide from resin. Then, the peptide was allowed to precipitate in diethyl ether. The crude peptide obtained by the above method was purified by using a purification-type reverse phase (RP)-HPLC column (Delta Pak, C18, 300 Å, 15, 19.0 mm×30 m, Waters, USA) based on acetonitrile gradient containing 0.05% TFA. The synthesized peptide was hydrolyzed with 6 N HCl at 110° C. Then, the resulting residues were concentrated under reduced pressure and dissolved in 0.02 N HCl. The amino acid composition was measured by using an amino acid analyzer (Hitachi 8500 Å). To determine the purity and molecular weight of the peptide, MALDI mass analysis (Hill, et al., Rapid Commun. Mass Spectrometry, 5: 395, 1991) was carried out.

As the result is shown in the following Table 1, the peptides represented by each amino acid sequence described with SEQ ID NO: 1 to SEQ ID NO: 15 were synthesized with purity of 95% or higher, and the molecular weight was found to be the same as the expected molecular weight.

TABLE 1

Sequence and molecular weight of peptides synthesized in the present invention

| Peptide name | Ammo acid sequence | SEQ ID NO: | Molecular Weight (Da) |
| --- | --- | --- | --- |
| Pseudin-2 | GLNALKKVFQGIHEAIKLINNHVQ-NH₂ | 1 | 2685.2 |
| Pse-11G-K | GLNALKKVFQKIHEAIKLINNHVQ-NH₂ | 2 | 2756.1 |

TABLE 1-continued

Sequence and molecular weight of peptides
synthesized in the present invention

| Name | Sequence | SEQ ID | MW |
|---|---|---|---|
| Pse-18L-K | GLNALKKVFQGIHEAIKKINNHVQ-NH$_2$ | 3 | 2700.1 |
| Pse-11G/18L-K | GLNALKKVFQKIHEAIKKINNHVQ-NH$_2$ | 4 | 2771.2 |
| Pse-Anal1 | WLNALKKVFQGIHEAIKLINNHVQ-NH$_2$ | 5 | 2814.3 |
| Pse-Anal2 | WLNALKKVFQGIHEAIKLIWNHVQ-NH$_2$ | 6 | 2886.4 |
| Pse-Anal3 | WLNALKKVFQGIHEAIKLIWNWVQ-NH$_2$ | 7 | 2935.5 |
| Pse-Anal4 | WLNALKKVWQGIHEAIKLIWNWVQ-NH$_2$ | 8 | 2974.5 |
| Pse-Anal5 | GLNALKKVSQGIHEAIKLINNHVQ-NH$_2$ | 9 | 2625.1 |
| Pse-Anal6 | GLNALKKVSQGIHESIKLINNHVQ-NH$_2$ | 10 | 2641.1 |
| Pse-Anal7 | ALNALKKVSQGIHEAIKLIANHVQ-NH$_2$ | 11 | 2595.7 |
| Pse-T1 | LNALKKVFQGIHEAIKLI-NH$_2$ | 12 | 2035.6 |
| Pse-T2 | LNALKKVFQKIHEAIKLI-NH$_2$ | 13 | 2106.6 |
| Pse-T3 | LNALKKVFQGIHEAIKKI-NH$_2$ | 14 | 2050.5 |
| Pse-T4 | LNALKKVFQKIHEAIKKI-NH$_2$ | 15 | 2121.7 |

| | Amino Acid NO. | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| Pseudin-2 | G | L | N | A | L | K | K | V | F | Q | G | I | H | E | A | I | K | L | I | N | N | H | V | Q |
| Pse-11G-K | – | – | – | – | – | – | – | – | – | – | K | – | – | – | – | – | – | – | – | – | – | – | – | – |
| Pse-18L-K | – | – | – | – | – | – | – | – | – | – | – | – | – | – | – | – | – | K | – | – | – | – | – | – |
| Pse-11G/18L-K | – | – | – | – | – | – | – | – | – | – | K | – | – | – | – | – | – | K | – | – | – | – | – | – |
| Pse-Anal1 | W | – | – | – | – | – | – | – | – | – | – | – | – | – | – | – | – | – | – | – | – | – | – | – |
| Pse-Anal2 | W | – | – | – | – | – | – | – | – | – | – | – | – | – | – | – | – | – | – | W | – | – | – | – |
| Pse-Anal3 | W | – | – | – | – | – | – | – | – | – | – | – | – | – | – | – | – | – | – | W | – | W | – | – |
| Pse-Anal4 | W | – | – | – | – | – | – | – | W | – | – | – | – | – | – | – | – | – | – | W | – | W | – | – |
| Pse-Anal5 | – | – | – | – | – | – | – | – | S | – | – | – | – | – | – | – | – | – | – | – | – | – | – | – |
| Pse-Anal6 | – | – | – | – | – | – | – | – | S | – | – | – | – | – | S | – | – | – | – | – | – | – | – | – |
| Pse-Anal7 | A | – | – | – | – | – | – | – | S | – | – | – | – | – | – | – | – | – | – | A | – | – | – | – |
| Pse-T1 | – | – | – | – | – | – | – | – | – | – | – | – | – | – | – | – | – | – | – | | | | | |
| Pse-T2 | – | – | – | – | – | – | – | – | – | – | K | – | – | – | – | – | – | – | – | | | | | |
| Pse-T3 | – | – | – | – | – | – | – | – | – | – | – | – | – | – | – | – | – | K | – | | | | | |
| Pse-T4 | – | – | – | – | – | – | – | – | – | – | K | – | – | – | – | – | – | K | – | | | | | |

[blank: deletion of amino acid, –: no substitution of amino acid]

Example 2. Measurement of Antimicrobial Activity

To compare the antimicrobial activity among the peptides produced by the method of Example 1, the inventors of the present invention measured the minimal growth inhibitory concentration (MIC), which is minimum concentration of the peptide not allowing any dissociation of bacterial cells.

Specifically, the bacterial strains described in the following Table 2 were purchased and cultured to a mid-log phase in a medium that is appropriate for each strain. Then, after dilution to bacterial cell concentration of $2 \times 10^4$ cells/100 µl, the cells were prepared on a microtiter plate (NUNC, USA). Thereafter, Pse-11G-K, Pse-18L-K, Pse-11G/18L-K, Pse-Anal1, Pse-Anal2, Pse-Anal3, Pse-Anal4, Pse-Anal5, Pse-Anal6, Pse-Anal7, Pse-T1, Pse-T2, Pse-T3, or Pse-T4 peptide which has been synthesized in Example 1 above was subjected to serial dilution, ½ times for each, in a 96-well plate. After the addition to a plate, the cells were cultured for 18 hours at 37° C. By using a microtiter plate reader (Merck Elisa reader, Germany), the absorbance was measured at a wavelength of 600 nm to determine the MIC value of each bacterial strain. As a control, Pseudin-2 as a mother peptide was used.

TABLE 2

Bacterial strains used in the present invention and sources of the bacterial strains

| Category | Name of bacterial strain | Source | Accession number |
|---|---|---|---|
| Gram-positive bacteria | Staphylococcus aureus | American Type Culture Collection | ATCC 25923 |
| | Bacillus subtilis | Korean Collection for Type Cultures | KCTC 1998 |
| | Listeria monocytogenes | Korean Collection for Type Cultures | KCTC 3710 |
| Gram-negative bacteria | Escherichia coli | American Type Culture Collection | ATCC 25922 |
| | Pseudomonas aeruginosa | American Type Culture Collection | ATCC 27853 |
| | Salmonella typhimurium | Korean Collection for Type Cultures | KCTC 1926 |
| Yeast | Candida albicans | Korean Collection for Type Cultures | KCTC 7270 |
| | Trichosporon beigelii | Korean Collection for Type Cultures | KCTC 7707 |
| Gram-positive bacteria having tolerance to antibiotics | Staphylococcus aureus | Culture Collection of Antimicrobial Resistant Microbes | CCARM 3518 |
| | | Culture Collection of Antimicrobial Resistant Microbes | CCARM 3090 |
| Gram-negative bacteria having tolerance to antibiotics | Escherichia coli | Culture Collection of Antimicrobial Resistant Microbes | CCARM 1229 |
| | | Culture Collection of Antimicrobial Resistant Microbes | CCARM 1238 |
| | Pseudomonas aeruginosa | Isolated strain 4007 | |
| | | Isolated strain 4891 | |

As a result, it was found in the following Table 3 that Pse-11G-K, Pse-18L-K, Pse-11G/18L-K, Pse-Anal1, Pse-Anal2, Pse-Anal3, Pse-Anal4, Pse-Anal5, Pse-Anal6, Pse-Anal7, Pse-T1, Pse-T2, Pse-T3, or Pse-T4 peptide exhibits an antimicrobial activity for Gram-positive bacteria, Gram-negative bacteria, and yeast, wherein the activity is the same or higher than the activity shown by Pseudin-2 as a mother peptide. In particular, compared to the mother peptide and other novel peptides, Pse-T1, Pse-T2, Pse-T3 and Pse-T4 peptides exhibited a significantly higher antimicrobial activity for yeast.

TABLE 3

Antimicrobial activity of antimicrobial peptides

| Strain | Pseudin-2 | Pse-11G-K | Pse-18L-K | Pse-11G/18L-K | Pse-Anal1 | Pse-Anal2 | Pse-Anal3 |
|---|---|---|---|---|---|---|---|
| Gram-positive bacteria | | | | | | | |
| S. aures | 22 | 4 | 8 | 8 | 32 | 4 | 32 |
| B. subtilis | 32 | 4 | 8 | 8 | 32 | 4 | 32 |
| L. monocytogenes | 32 | 8 | 8 | 8 | 32 | 8 | 32 |
| Gram-negative bacteria | | | | | | | |
| E. coli | 16 | 2 | 4 | 4 | 16 | 2 | 16 |
| P. aeruginosa | 16 | 2 | 2 | 2 | 16 | 2 | 16 |
| S. typhimurium | 16 | 2 | 4 | 4 | 16 | 2 | 16 |
| Yeast | | | | | | | |
| C. albicans | 32 | 32 | 32 | 32 | 64 | 32 | 32 |
| T. beigelii | 22 | 32 | 32 | 32 | 64 | 32 | 32 |
| Gram-positive bacteria having tolerance to antibiotics | | | | | | | |
| S. aureus 3518 | 32 | 4 | 8 | 4 | 32 | 4 | 32 |
| S. aureus 3090 | 32 | 4 | 8 | 8 | 32 | 4 | 32 |
| Gram-negative bacteria having tolerance to antibiotics | | | | | | | |
| E. coli 1229 | 16 | 2 | 4 | 4 | 16 | 2 | 32 |
| E. coli 1238 | 16 | 2 | 4 | 4 | 16 | 2 | 32 |
| P. aeruginosa 4007 | 16 | 2 | 2 | 2 | 16 | 2 | 64 |
| P. aeruginosa 4891 | 16 | 4 | 8 | 4 | 16 | 4 | 64 |

| Strain | Pse-Anal4 | Pse-Anal5 | Pse-Anal6 | Pse-Anal7 | Pse-T1 | Pse-T2 | Pse-T3 | Pse-T4 |
|---|---|---|---|---|---|---|---|---|
| Gram-positive bacteria | | | | | | | | |
| S. aures | 32 | 32 | 32 | 16 | 8 | 4 | 4 | 4 |
| B. subtilis | 32 | 32 | 32 | 16 | 8 | 4 | 4 | 8 |
| L. monocytogenes | 32 | 32 | 32 | 16 | 8 | 4 | 8 | 8 |

TABLE 3-continued

| Antimicrobial activity of antimicrobial peptides | | | | | | | | |
|---|---|---|---|---|---|---|---|---|
| Gram-negative bacteria | | | | | | | | |
| E. coli | 16 | 16 | 16 | 8 | 4 | 2 | 2 | 2 |
| P. aeruginosa | 16 | 16 | 16 | 8 | 4 | 2 | 4 | 4 |
| S. typhimurium | 16 | 16 | 16 | 8 | 4 | 2 | 4 | 4 |
| Yeast | | | | | | | | |
| C. albicans | 32 | 64 | 64 | 32 | 16 | 16 | 16 | 16 |
| T. beigelii | 32 | 64 | 64 | 32 | 16 | 8 | 16 | 16 |
| Gram-positive bacteria having tolerance to antibiotics | | | | | | | | |
| S. aureus 3518 | 32 | 64 | 64 | 32 | 8 | 4 | 4 | 4 |
| S. aureus 3090 | 32 | 64 | 64 | 32 | 8 | 4 | 4 | 4 |
| Gram-negative bacteria having tolerance to antibiotics | | | | | | | | |
| E. coli 1229 | 32 | 32 | 64 | 16 | 4 | 2 | 2 | 2 |
| E. coli 1238 | 32 | 32 | 64 | 16 | 4 | 2 | 2 | 2 |
| P. aeruginosa 4007 | 64 | 64 | 64 | 32 | 4 | 2 | 4 | 4 |
| P. aeruginosa 4891 | 64 | 64 | 64 | 32 | 8 | 4 | 8 | 4 |

Example 3. Measurement of Hemolytic Activity

To compare the cytotoxicity among the peptides that are produced by the method of Example 1, erythrocyte hemolytic activity of the synthesized peptide was measured.

Specifically, erythrocytes of a mouse (Balb/c, 6 week old, female) were diluted in PBS (pH 7.0) to have concentration of 8%, and then subjected to a treatment with Pseudin-2, Pse-11G-K, Pse-18L-K, Pse-11G/18L-K, Pse-Anal1, Pse-Anal2, Pse-Anal3, Pse-Anal4, Pse-Anal5, Pse-Anal6, Pse-Anal7, Pse-T1, Pse-T2, Pse-T3, or Pse-T4 peptide, at concentration of 6.25, 12.5, 25.0, 50.0, and 100.0 μM/well for each, followed by a reaction for 1 hour at 37° C. After that, the amount of hemoglobin contained in a supernatant collected by centrifuge at 1,000×g was determined by measuring the absorbance at a wavelength of 414 nm. As a control to be used as a reference for cell disruption level, the supernatant collected by a treatment with 1% Triton X-100 (Sigma, USA) and a reaction for 1 hour at 37° C. was used to measure the absorbance. By setting the resulting absorbance value at 100% of the erythrocyte hemolytic activity, hemolysis of each peptide was calculated using the following equation 1.

Erythrocyte disrupting ability (%)=(Absorbance $A$–Absorbance $B$)/(Absorbance $C$–Absorbance $B$)×100    Equation 1

(in the above equation, Absorbance A indicates the absorbance of a reaction solution treated with each peptide, in which the absorbance is measured at a wavelength of 414 nm; Absorbance B indicates the absorbance of a reaction solution treated with PBS, in which the absorbance is measured at a wavelength of 414 nm; and Absorbance C indicates the absorbance of a reaction solution treated with 1% Triton X-100, in which the absorbance is measured at a wavelength of 414 nm).

As the result is shown in Table 4, it was found that, when mouse erythrocytes are treated with 100 μM Pseudin-2 peptide as a mother peptide, hemolytic activity was shown to be only 10%. Meanwhile, Pse-11G-K, Pse-Anal1, Pse-Anal2, Pse-Anal3 and Pse-Anal4 peptides exhibited erythrocyte hemolytic activity of 100% even at the concentration of 100 μM, indicating higher toxicity. However, Pse-T1, Pse-T2, Pse-T3 and Pse-T4, in which amino acids have been deleted, exhibited the same or lower hemolytic activity than the mother peptide. It was therefore found that, compared to the mother peptide, the antimicrobial peptides of the present invention exhibit higher antimicrobial activity while having similar or lower cytotoxicity.

TABLE 4

Hemolytic activity of antimicrobial peptides

| | Erythrocyte disrupting ability % (peptide concentration, μM) | | | | | |
|---|---|---|---|---|---|---|
| | 100 | 50 | 25 | 12.5 | 6.25 | 3.13 |
| Pseudin-2 | 10.1 | 3.2 | 0 | 0 | 0 | 0 |
| Pse-11G-K | 99.2 | 97.8 | 84.0 | 69.8 | 49.4 | 17.3 |
| Pse-18L-K | 36.7 | 24.2 | 12.5 | 5.4 | 3.4 | 2.4 |
| Pse-11G/18L-K | 18.0 | 6.6 | 1.3 | 0.7 | 0 | 0 |
| Pse-Anal1 | 100 | 93.5 | 82.0 | 68.9 | 58.6 | 50.9 |
| Pse-Anal2 | 88.6 | 86.7 | 78.6 | 65.0 | 58.5 | 45.5 |
| Pse-Anal3 | 100 | 100 | 100 | 100 | 85.6 | 76.6 |
| Pse-Anal4 | 100 | 100 | 99.5 | 92.9 | 84.5 | 70.8 |
| Pse-Anal5 | 20.1 | 11.7 | 5.9 | 2.3 | 0.7 | 0 |
| Pse-Anal6 | 1.4 | 0.5 | 0.2 | 0 | 0 | 0 |
| Pse-Anal7 | 0.1 | 0 | 0 | 0 | 0 | 0 |
| Pse-T1 | 12.3 | 3.9 | 0 | 0 | 0 | 0 |
| Pse-T2 | 15.2 | 4.7 | 0 | 0 | 0 | 0 |
| Pse-T3 | 5.6 | 2.2 | 0.5 | 0 | 0 | 0 |
| Pse-T4 | 1.3 | 0 | 0 | 0 | 0 | 0 |

Example 4. Determination of Cytotoxicity in Normal Cell Line

To determine the cytotoxicity of the peptides produced by the method of Example 1 in normal cell line, cytotoxicity was measured by using human keratinocyte cell line (HaCaT cell line, Dr. N E. Fusenig, Heidelberg, Germany).

Specifically, HaCaT cells, which have been cultured in DMEM medium containing 10% FBS (fetal bovine serum), were aliquoted in a microtiter plate to have $2 \times 10^5$ cells per well. After culturing them for 24 hours, the cells were subjected to a treatment with Pseudin-2, Pse-11G-K, Pse-18L-K, Pse-11G/18L-K, Pse-Anal1, Pse-Anal2, Pse-Anal3, Pse-Anal4, Pse-Anal5, Pse-Anal6, Pse-Anal7, Pse-T1, Pse-T2, Pse-T3, or Pse-T4 peptide, each at concentration of 6.25, 12.5, 25.0, 50.0 or 100.0 μM/well, followed by reaction for 24 hours in a 5% $CO_2$ incubator. Twenty-four hours later, a reaction solution containing 0.5 mg/ml MTT (thiazolyl blue tetrazolium bromide) dissolved in phosphate buffered saline (PBS) was added in an amount of 100 μl to each well and the reaction was allowed to occur for 4 hours. After that, the supernatant was discarded, and, by dissolving MTT crystals that are formed by adding 200 µl DMSO (dimethyl sulfoxide), the absorbance at 560 nm was measured to determine the cell survival ability.

As a result, it was found as shown in the following Table 5 that, when the cells are treated with Pseudin-2 peptide as a mother peptide (100 µM), HaCaT cells showed the cell survival ability of 82.1%, indicating that Pseudin-2 peptide exhibits low cytotoxicity. Meanwhile, when treated with Pse-11G-K, Pse-Anal1, Pse-Anal2, Pse-Anal3, or Pse-Anal4 peptide, HaCaT cells exhibited the cell survival ability of 36.4%, 1.8%, 5.1%, 10.8% and 10.1%, respectively, even at a peptide concentration of 100 µM, indicating that they exhibit very high cytotoxicity. However, Pse-T1, Pse-T2, Pse-T3 and Pse-T4, in which amino acids have been deleted, exhibited the same or lower cytotoxicity than the mother peptide. It was therefore found that, compared to the mother peptide, the antimicrobial peptides of the present invention exhibit higher antimicrobial activity while having similar or lower cytotoxicity.

TABLE 5

Analysis of cytotoxicity of antimicrobial peptides

| | Cell survival ability % (peptide concentration, µM) | | | | | |
|---|---|---|---|---|---|---|
| | 100 | 50 | 25 | 12.5 | 6.25 | 3.13 |
| Pseudin-2 | 82.1 | 100 | 100 | 100 | 100 | 100 |
| Pse-11G-K | 36.4 | 50.2 | 73.8 | 100 | 100 | 100 |
| Pse-18L-K | 81.5 | 100 | 100 | 100 | 100 | 100 |
| Pse-11G/18L-K | 91.3 | 100 | 100 | 100 | 100 | 100 |
| Pse-Anal1 | 1.8 | 13.6 | 15.9 | 26.8 | 35.2 | 80.1 |
| Pse-Anal2 | 5.1 | 15.7 | 18.8 | 32.2 | 48.1 | 81.3 |
| Pse-Anal3 | 10.8 | 13.6 | 24.1 | 25.6 | 45.8 | 55.4 |
| Pse-Anal4 | 10.8 | 15.3 | 20.8 | 25.4 | 35.1 | 46.1 |
| Pse-Anal5 | 83.5 | 96.3 | 100 | 100 | 100 | 100 |
| Pse-Anal6 | 92.1 | 100 | 100 | 100 | 100 | 100 |
| Pse-Anal7 | 100 | 100 | 100 | 100 | 100 | 100 |
| Pse-T1 | 86.2 | 98.8 | 100 | 100 | 100 | 100 |
| Pse-T2 | 79.4 | 95.3 | 100 | 100 | 100 | 100 |
| Pse-T3 | 90.3 | 100 | 100 | 100 | 100 | 100 |
| Pse-T4 | 96.5 | 100 | 100 | 100 | 100 | 100 |

Example 5. Measurement of Circular Dichroism Spectrum

To determine whether or not an α-helical structure as a secondary structure is induced by the peptides produced by the method of Example 1, measurement was carried out using circular dichroism.

Specifically, Pseudin-2, Pse-11G-K, Pse-18L-K, Pse-11G/18L-K, Pse-Anal1, Pse-Anal2, Pse-Anal3, Pse-Anal4, Pse-Anal5, Pse-Anal6, Pse-Anal7, Pse-T1, Pse-T2, Pse-T3, or Pse-T4 peptide was added at a concentration of 40 µM to 10 mM PBS (pH 7.4), or to 1 mM large unilamellar vesicles (LUV) composed of PE/PG (L-α-phosphatidylethanolamine/L-α-phosphatidyl-DL-glycerol; 7/3, w/w) or PC/CH/SM (L-α-phosphatidylcholine/cholesterol/sphingomyelin; 1/1/1, w/w/w) in a cell with 0.1 cm path length. Then, a circular dichroism spectrum was measured by using Jasco 810 spectrophotometer of which temperature has been set at 25° C. As an equation to calculate an α-helical structure for the above circular dichroism spectrum, the following equation 2 was used.

$$[\theta] = \frac{\theta_{obs}}{10 \cdot l \cdot c} \quad \text{Equation 2}$$

(in the equation, $\theta_{obs}$ represents the millidegrees of a signal; l represents the optical path-length of a cell (cm); and c represents the concentration of added peptide (mol/l)).

As a result, no secondary structure was formed when the peptide was added to the 10 mM PBS solution. However, when the peptide was added to LUV solution composed of PE/PG (7/3) or PC/CH/SM (1/1/1), it was found that an α-helical structure. i.e., secondary structure, was formed with every peptide, even though there was a variation in the forming degree. Based on those results, it was found that an α-helical structure is formed by the antimicrobial peptides of the present invention in PE/PG (7/3) solution which is similar to a membrane of bacteria as microorganism and also in PC/CH/SM (1/1/1) solution which is similar to a membrane of an eukaryote (FIG. 1).

Example 6. Flow Cytometry Measurement

To determine whether or not the peptides prepared by the method of Example 1 exhibit any effect on bacteria membrane, an analysis was made by flow cytometry using Pse-T1, Pse-T2, Pse-T3 and Pse-T4 peptides, which have been found to have higher antimicrobial activity than mother peptide but exhibit no cytotoxicity even at high concentrations.

Specifically, Escherichia coli or Staphylococcus aureus was treated with mother Pseudin-2 peptide, or Pse-T1, Pse-T2, Pse-T3, or Pse-T4 peptide (at concentration of minimal growth inhibitory concentration (MIC)), and then the reaction was allowed to occur for 1 hour at 37° C. After that, the supernatant was removed by centrifuge (10,000 rpm) and stained with propidium iodide (PI, concentration of 10 µg/ml) for 30 minutes at 4° C. Thereafter, unbound propidium iodide was removed by centrifuge, and the problem of cell aggregation phenomenon was solved by adding physiological saline (PBS) in an amount of 1 ml. Then, by using Bechman flow cytometry, the effect of the peptides exhibited on bacteria membrane was determined.

As a result, it was found that, for Escherichia coli or Staphylococcus aureus cells, Pse-T1, Pse-T2, Pse-T3 and Pse-T4 peptides have higher membrane disrupting ability than Pseudin-2. In addition, among those peptides, Pse-T2 exhibited the highest membrane disrupting ability, i.e., 92% for Escherichia coli and 96% for Staphylococcus aureus. Based on the results, it was recognized that the novel peptides of the present invention have higher ability of disrupting bacteria membrane compared to the mother peptides as a control.

Example 7. Analysis of Binding Between Antimicrobial Peptide and DNA

To specifically determine the mechanism of exhibiting antimicrobial activity by the antimicrobial peptides of the present invention, binding between the synthetic peptides Pseudin-2, Pse-T1, Pse-T2, Pse-T3 and Pse-T4 and DNA, which is a substance present inside a bacteria cell, was examined by electrophoresis.

Specifically, plasmid DNA (pRSETB, 300 ng) and the peptide were reacted for at different ratio (i.e., peptide/DNA ratio was 0 (DNA only), 0.25:1, 0.5:1, 1:1, 1.5:1, 2:1, 3:1, or 4:1) for 10 minutes at 37° C. After that, electrophoresis was carried out using 1% agarose gel followed by staining with ethidium bromide (EtBr) and UV determination.

Figure 3:
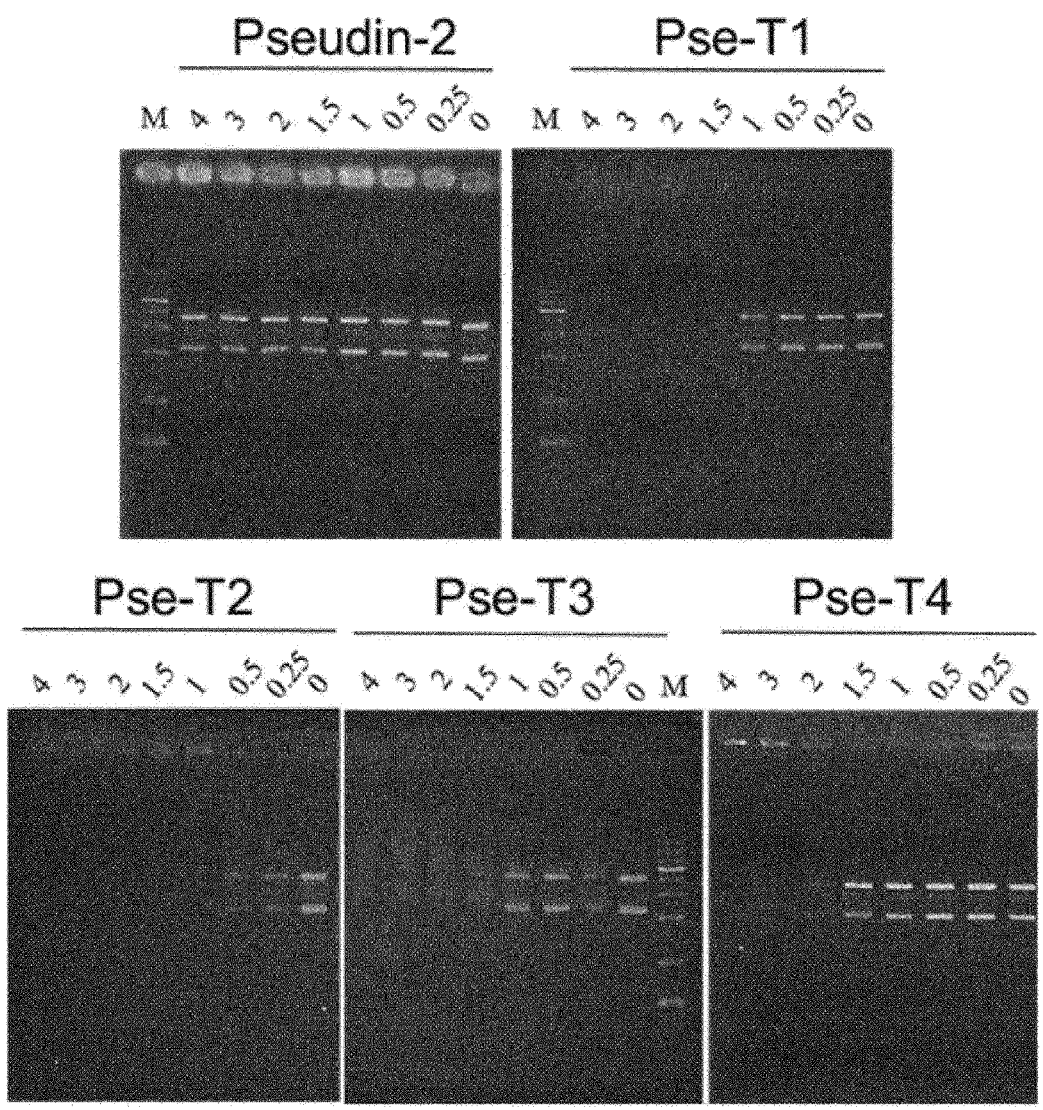
FIG. 3 illustrates the result of determining the binding activity of Pseudin-2 peptide as a control and novel peptides Pse-T1, Pse-T2, Pse-T3 and Pse-T4 for DNA as an internal material of bacteria, in which the peptide:DNA ratio is 0 (DNA only), 0.25:1, 0.5:1, 1:1, 1.5:1, 2:1, 3:1, or 4:1.

As the result is shown in FIG. 3, Pseudin-2 peptide did not show any binding to DNA while Pse-T1, Pse-T2, Pse-T3 and Pse-T4 all showed binding to DNA although the binding degree is different among them (FIG. 3). Based on the results, it was recognized that, unlike the mother peptide Pseudin-2 which exhibits the antimicrobial activity based on its action on bacteria membrane, Pse-T1, Pse-T2, Pse-T3 and Pse-T4 peptides exhibit their antimicrobial activity by binding to DNA as a substance present inside bacteria, in which the antimicrobial activity is caused by deletion or substitution of their amino acid residues.

Example 8. Scanning Electron Microscopy (SEM) Analysis

To determine whether or not the synthetic peptides of the present invention have any damaging effect on bacteria membrane, an analysis was made by scanning electron microscopy.

Specifically, *Escherichia coli* and *Staphylococcus aureus* cells were suspended in PBS at concentration of $OD_{600}=0.2$, treated with the mother Pseudin-2 peptide or Pse-T1, Pse-T2, Pse-T3 and Pse-T4 peptide at MIC, and reacted for 1 hour at 37° C. As a control, cells applied with no peptide were used. After the culture, the cells were collected, and, by using 2.5% glutaraldehyde, the bacterial cells were treated for 18 hour at 4° C. After carrying out washing two times with PBS buffer solution, the fixed cells were dehydrated in stepwise manner by using 100% ethanol and diluted ethanol (50%, 70%, 90% and 100%). After the dehydration followed by drying, the specimen was coated with platinum and determination was made by low vacuum scanning electron microscopy.

Figure 4:
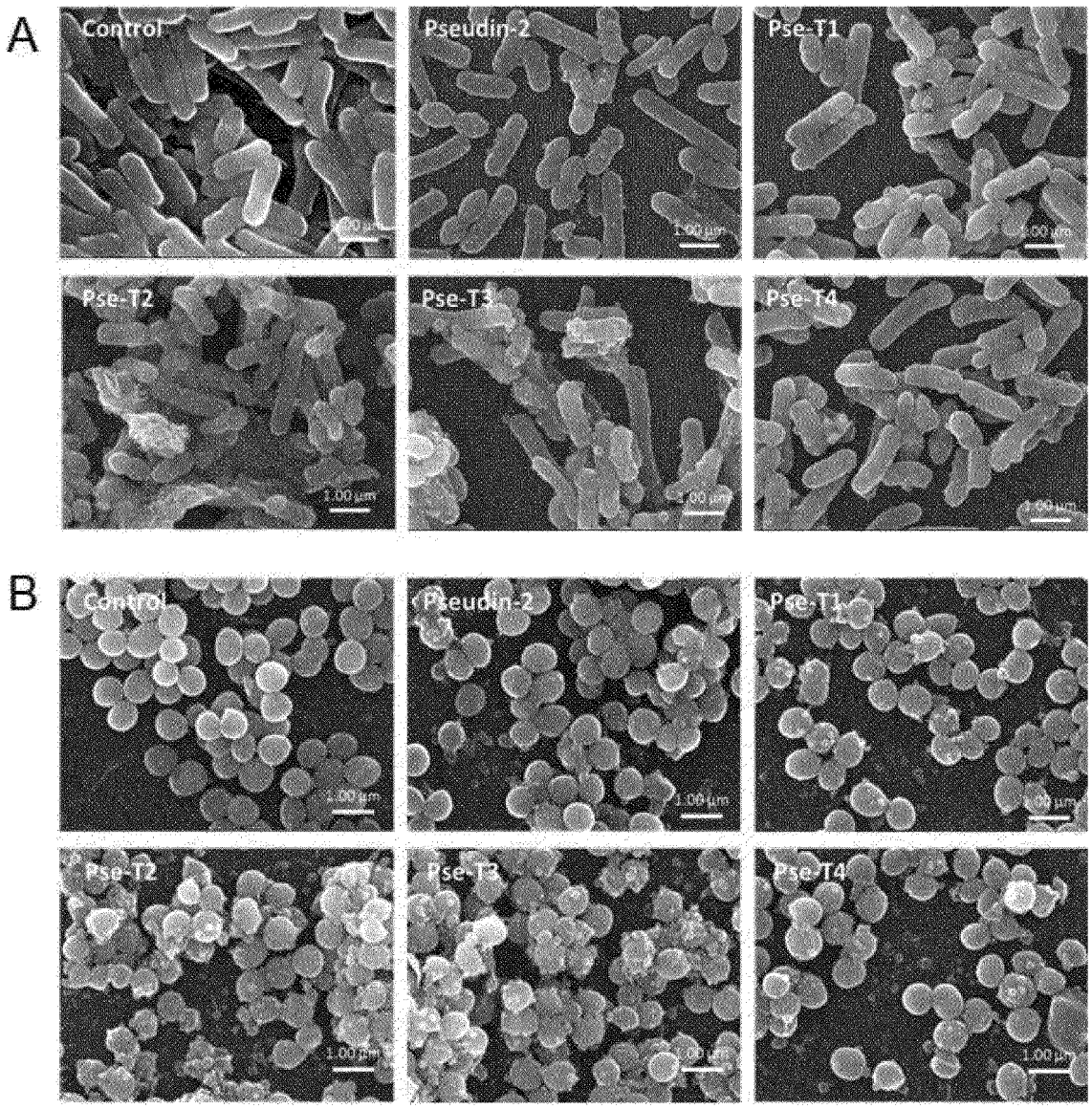
FIG. 4 illustrates the result of determining the action of Pseudin-2 peptide as a control and novel peptides Pse-T1, Pse-T2, Pse-T3 and Pse-T4 on the membrane of (A) *Escherichia coli* and (B) *Staphylococcus aureus*, in which the determination was made by scanning electron microscopy (SEM).

As the result is shown in FIG. 4, it was found that the control cells without any treatment have a bright and smooth surface while the cells with the treatment show a considerable amount of membrane damage. Surface of *Escherichia coli* treated with Pse-T2 or Pse-T3 peptide was rougher than the cells treated with Pseudin-2, and it showed a higher number of small sacs on the surface. It was observed that the cell surface exposed to the peptide have holes and blister-like damages. In some cells, substances contained in the cell cytoplasm were released. It was also found from the *Staphylococcus aureus* cells that, similar to *Escherichia coli*, higher damage and disruption of cell membrane is shown when the cells were treated with Pse-T2 or Pse-T3 compared to Pseudin-2, Pse-T1 or Pse-T4.

Example 9. Measurement of Antibiofilm Activity

The inventors of the present invention measured the biofilm inhibitory concentration value of Pse-T2, which exhibited the highest antimicrobial activity among the peptides produced by the method of Example 1.

Specifically, among the bacterial strains described in the above Table 2, *Staphylococcus aureus, Escherichia coli*, and *Pseudomonas aeruginosa* were cultured to a mid-log phase in each medium. Then, after dilution to bacterial cell concentration of $5\times10^4$ cells/100 μl, the cells were inoculated to a microplate (SPL). Thereafter, Pse-T2 peptide was diluted, ⅒ times for each, with 10 mM PBS (pH 7.2) in each well. After adding the peptide (10 μl) to each well of the plate, the cells were cultured for 24 hours at 37° C. After removing the supernatant completely, the cells were fixed with 100% methanol for 15 minutes and stained for 1 hour with Crystal violet staining solution followed by rinsing for 3 times. Then, after dissolving in 95% ethanol, the absorbance was measured at a wavelength of 595 nm by using a microtiter plate reader to determine the biofilm minimal inhibitory concentration value of each bacterial strain.

As the result is shown in the following Table 6, Pse-T2 peptide was found to exhibit a strong biofilm inhibitory activity in all bacterial cells compared to ciprofloxacin as a control antibiotic.

TABLE 6

Antibiofilm activity of antimicrobial peptides for Gram-negative bacteria, Gram-positive bacteria, and bacteria having tolerance to antibiotics

| | Biofilm minimal inhibitory concentration (μM) | |
|---|---|---|
| | Pse-T2 | Ciprofloxacin |
| Gram-positive bacteria | | |
| *S. aureus* (ATCC 25923) | 8 | 4 |
| *S. aureus* (CCARM 3518) | 16 | >400 |
| *S. aureus* (CCARM 3090) | 32 | >400 |
| Gram-negative bacteria | | |
| *E. coli* (ATCC 25922) | 4 | 2 |
| *E. coli* (CCARM 1229) | 8 | 128 |
| *E. coli* (CCARM 1238) | 16 | 128 |
| *P. aeruginosa* (ATCC 27853) | 4 | 2 |
| *P. aeruginosa* 4007 | 8 | >400 |
| *P. aeruginosa* 4891 | 16 | >400 |

Example 10. Measurement of Ability of Healing Lesion Infected with Multi-Drug Resistant *Pseudomonas aeruginosa*

By using a mouse model, inventors of the present invention examined, in vivo, the effect of Pse-T2, which is the peptide exhibiting the highest antimicrobial activity among the peptides prepared by the method of Example 1 above.

Specifically, outer skin of the backside of a 6 to 7 week-old BALB/c mouse was rubbed with sandpaper to induce a skin lesion, which was then infected with *Pseudomonas aeruginosa* (*P. aeruginosa*) 4891 ($1\times10^8$ CFU/20 μl PBS). Two hours after the infection, the animal was injected with antimicrobial peptide Pse-T2 (0.2 mg/kg, 20 μl). For a control mouse, peptide-free PBS in the same volume as above (20 μl) was injected. On Day 3, Day 4, Day 5, Day 6, Day 7, and Day 10 after the injection, shape of the lesion was photographed, size of the lesion was measured, and tissues were collected from the lesion and surrounding area. The tissues with lesion were homogenized in PBS (500 μl) using a tissue homogenizer. A serial dilution product of the homogenate was plated on an agar plate, cultured for 24 hours, and then *Pseudomonas aeruginosa* 4891 bacteria were quantified.

Figure 5:
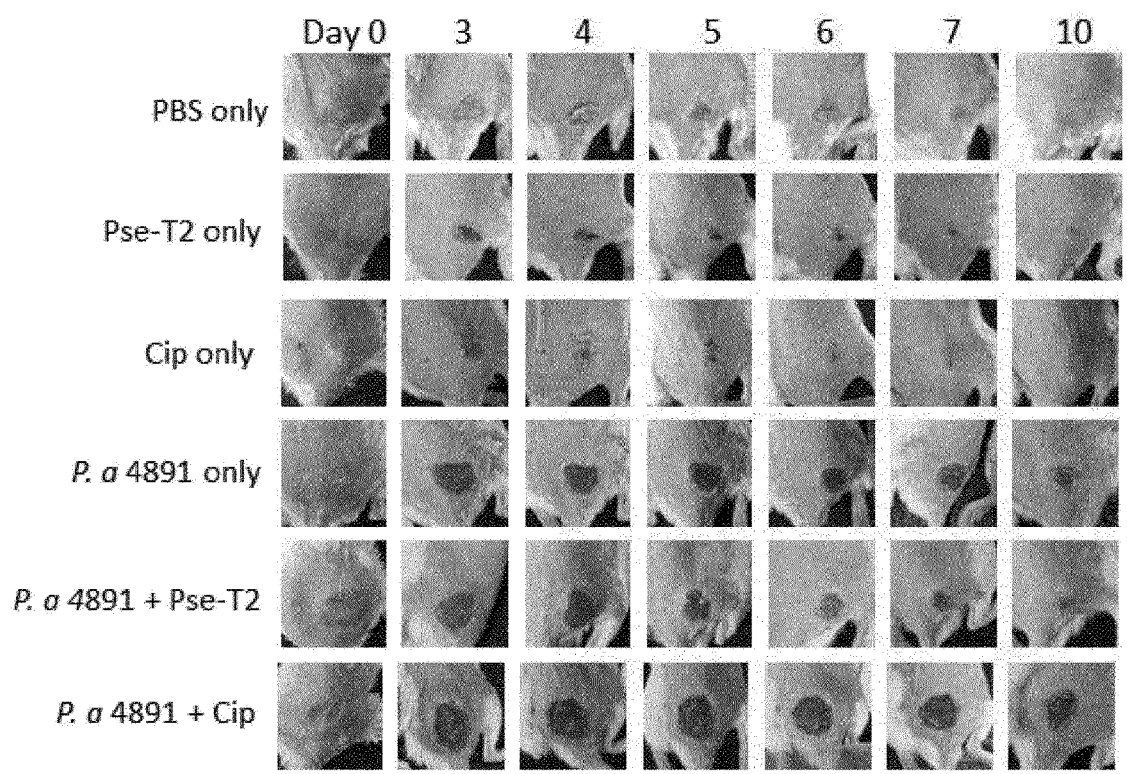
FIG. 5 illustrates the result of determining the therapeutic effect of Pse-T2 for a lesion caused by infection with *Pseudomonas aeruginosa* 4891, which is a multi-drug resistant bacterium.
Figure 6:
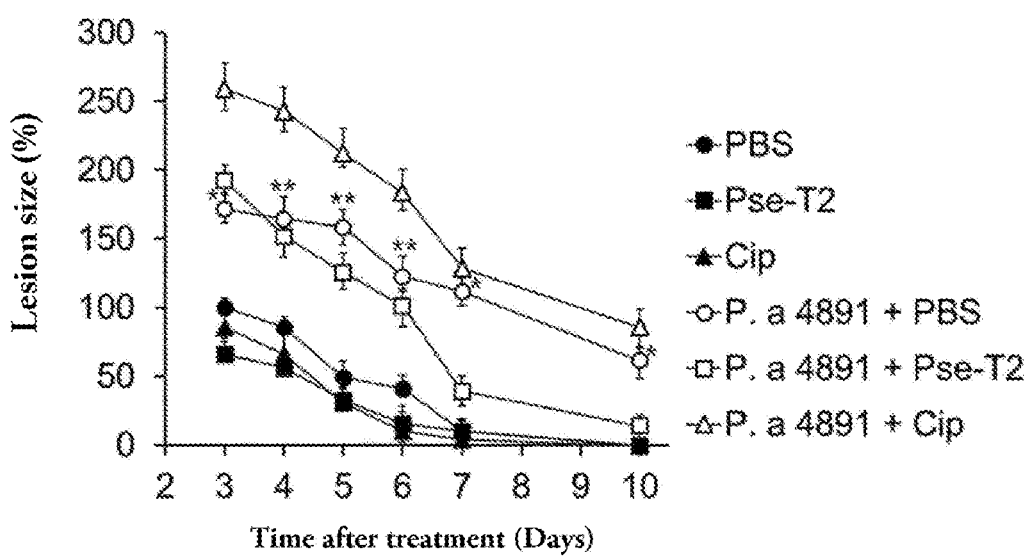
FIG. 6 illustrates the result of determining a change in the size of a lesion caused by infection with *Pseudomonas aeruginosa* 4891, which is a multi-drug resistant bacterium.
Figure 7:
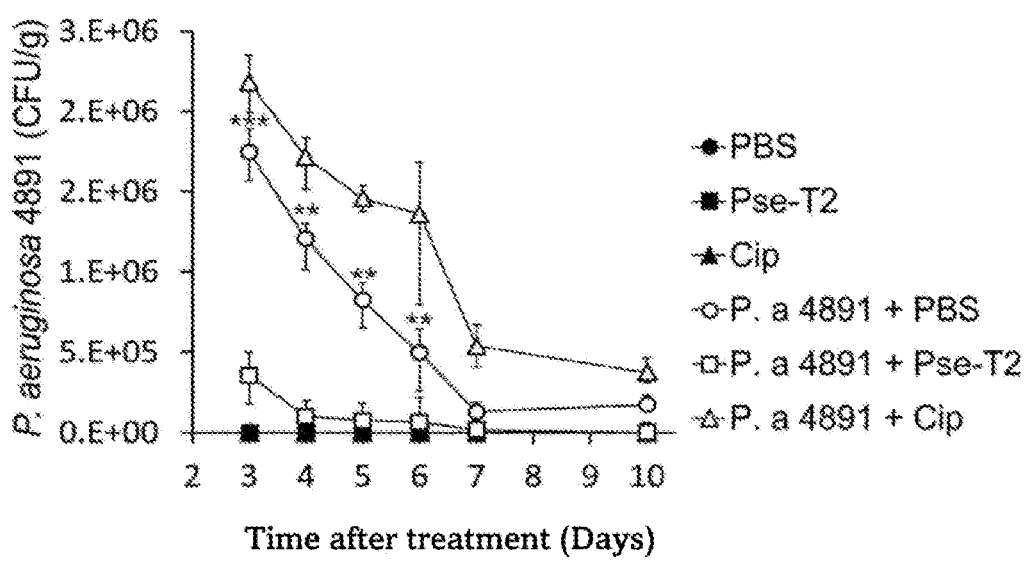
FIG. 7 illustrates the result of determining the total count of recovered cells (CFU/g), which have been obtained by collecting the lesion infected with *Pseudomonas aeruginosa* 4891, which is a multi-drug resistant bacterium.

As a result, the test group injected with PBS only, i.e., no infection with *Pseudomonas aeruginosa* 4891, the test group injected with Pse-T2 only, and the test group injected with ciprofloxacin only all showed complete healing of lesion within 6 to 8 days (FIG. 5). Meanwhile, the lesion infected with *Pseudomonas aeruginosa* 4891 was larger than the case without having any bacterial infection on the same date, and the infected lesion maintained the same size till Day 6, indicating severe inflammation in the lesion. On the contrary, in the test group treated with Pse-T2 peptide following the infection with *Pseudomonas aeruginosa* 4891, the lesion was healed at level of 41 to 54% approximately after Day 6. In addition, after Day 10, the lesion was healed at level of 90% to 92% (FIGS. 5 and 6). According to the result of determining the bacteria count after culturing the homogenate of lesion tissues, it was also found that, compared to the treatment with PBS after bacteria infection, less bacteria count of *Pseudomonas aeruginosa* 4891 is obtained when the lesion was treated with Pse-T2 peptide after bacteria infection, i.e., at least 80% or at least 95% less than the PBS treatment, on Day 3 and on Day 6, respectively (FIG. 7). Based on the results, it was recognized that Pse-T2 peptide is effective for healing a lesion.

Example 11. Analysis of Proinflammatory Cytokine Gene Expression Using Quantitative Real-Time PCR A change in mRNA expression of inflammatory mediators like interleukin-1 beta (IL-1β), interleukin-6 (IL-6), and tumor necrosis factor-alpha (TNF-α) occurs when skin is infected or a lesion is healed. By measuring the expression of inflammatory genes in a mouse not infected with any bacteria, a mouse infected with bacteria, and a mouse administered with Pse-T2 peptide after the infection, effect of Pse-T2 was determined.

Specifically, total RNA was isolated from lesion tissues by using TRIzol reagent, cDNA was then synthesized from the prepared total RNA by using a kit for cDNA synthesis. qPCR was carried out by using qPCR 2× premix (SYBR Green) and, among the inflammatory genes, expression amount of IL-1β, IL-6 and TNF-α was examined. The expression level was quantified by using β-actin as a reference. PCR process was carried out as follows: 2 minutes at 50° C., 10 minutes at 95° C.; 15 seconds at 95° C., 1 minute at 60° C., 40 cycles; 15 seconds at 95° C., 1 minute at 60° C. and 30 seconds at 95° C., 15 seconds at 60° C.

Figure 8:
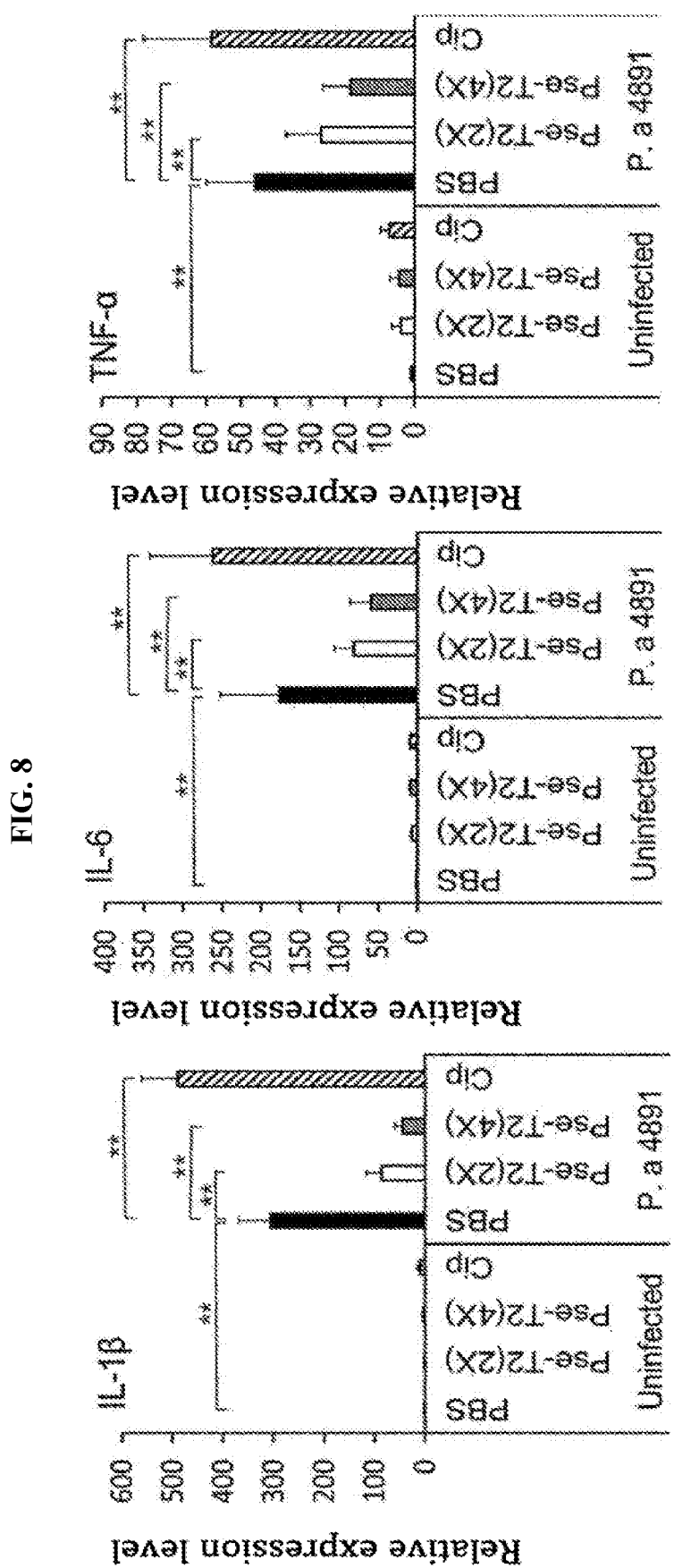
FIG. 8 illustrates the result of determining relative expression level of the genes that are associated with an inflammation response in tissues having lesion caused by infection with *Pseudomonas aeruginosa* 4891, which is a multi-drug resistant bacterium, in which IL-1β: interleukin-1 beta, IL-6: interleukin-6, and TNF-α: tumor necrosis factor-alpha.

As a result of determining the mRNA expression of IL-1β, IL-6, and TNF-α, it was observed that expression of each inflammatory cytokine has increased in skin lesion infected with *Pseudomonas aeruginosa* 4891, and the expression of inflammatory cytokine was suppressed when the skin lesion infected with bacteria is treated with Pse-T2 peptide (FIG. 8). Based on this result, it was found that the expression of inflammatory cytokines, which have been induced in a mouse by bacterial infection, is suppressed by Pse-T2 peptide. It was therefore recognized that, in a living body, the antimicrobial effect against *Pseudomonas aeruginosa* 4891 is exhibited and also inflammation appeared to be a response to bacterial infection can be suppressed by a treatment with Pse-T2.

Hereinbelow, production examples for producing the composition of the present invention are exemplified.

<Production Example 1> Production of Pharmaceutical Preparation

<1-1> Production of Powder Preparation

| | |
|---|---|
| Peptide of the present invention | 20 mg |
| Lactose | 20 mg |

After mixing the above components, a powder preparation was produced by filling them in a sealed pack.

<1-2> Production of Tablet

| | |
|---|---|
| Peptide of the present invention | 10 mg |
| Corn starch | 100 mg |
| Lactose | 100 mg |
| Magnesium stearate | 2 mg |

After mixing the above components, a tablet was produced according to tabletting by a common method for producing a tablet.

<1-3> Production of Capsule Preparation

| | |
|---|---|
| Peptide of the present invention | 10 mg |
| Crystalline cellulose | 3 mg |
| Lactose | 14.8 mg |
| Magnesium stearate | 0.2 mg |

After mixing the above components, a capsule preparation was produced according to filling them in a gelatin capsule by a common method for producing a capsule preparation.

<1-4> Production of Liquid Preparation

| | |
|---|---|
| Peptide of the present invention | 20 mg |
| High fructose corn syrup | 10 g |
| Mannitol | 5 g |
| Purified water | suitable amount |

According to a common method for producing a liquid preparation, each component was added to purified water for dissolution. After adding a suitable amount of lemon flavor, the above components were admixed with one another followed by addition of purified water to adjust the entire volume to 100 ml. The mixture was then filled in a brown bottle followed by sterilization to produce a liquid preparation.

<1-5> Production of Injection Solution

| | |
|---|---|
| Peptide of the present invention | 10 μg/ml |
| Dil. hydrochloric acid BP | till to have pH 7.6 |
| Sodium chloride BP for injection | 1 ml at maximum |

In sodium chloride BP for injection with suitable volume, the peptide of the present invention was dissolved. pH of the resulting solution was adjusted to pH 7.6 by using dil. hydrochloric acid BP, and the volume was adjusted by using sodium chloride BP for injection followed by thorough mixing. The resulting solution was filled in a 5 ml Type I ampoule made of transparent glass. By melting the glass, the ampoule was sealed while having air in the top. Then, according to autoclave for 15 minutes or longer at 120° C., sterilization was carried out to produce an injection solution.

<Production Example 2> Production of Cosmetics

<2-1> Softening Cosmetic Water (Skin Lotion)

To produce an antimicrobial softening cosmetic water containing the peptide of the present invention, blending can be carried out as described in the following Table 7 and production can be made according to a common production method in the cosmetic field.

TABLE 7

Softening cosmetic water composition

| Component | Content (% by weight) |
| --- | --- |
| Peptide of the present invention | 0.1 to 30 |
| 1,3-Butylene glycol | 3.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-2> Nutritive Cosmetic Water (Lotion)

To produce an antimicrobial nutritive cosmetic water containing the peptide of the present invention, blending can be carried out as described in the following Table 8 and production can be made according to a common production method in the cosmetic field.

TABLE 8

Nutritive cosmetic water composition

| Component | Content (% by weight) |
| --- | --- |
| Peptide of the present invention | 0.1 to 30 |
| Squalane | 10.0 |
| Monooleic acid polyoxyethylene sorbitan | 2.0 |
| Lignum vitae oil | 0.1 to 30 |
| 1,3-Butylene glycol | 8.0 |
| Glycerin | 5.0 |
| Polyoxyethylene (60) hydrogenated castor oil | 0.2 |
| Ethanol | 8.0 |
| Citric acid | 0.02 |
| Sodium citrate | 0.06 |
| Preservative | trace amount |
| Fragrance | trace amount |
| Purified water | To 100 |

<2-3> Essence

To produce an antimicrobial essence containing the peptide of the present invention, blending can be carried out as described in the following Table 9 and production can be made according to a common production method in the cosmetic field.

TABLE 9

Essence composition

| Component | Content (% by weight) |
| --- | --- |
| Peptide of the present invention | 0.1 to 30 |
| Sitosterol | 1.7 |
| Polyglyceryl 2-oleate | 1.5 |
| Ceramide | 0.7 |
| Ceteareth-4 | 1.2 |
| Cholesterol | 1.5 |
| Dicetyl phosphate | 0.4 |
| Conc. glycerin | 5.0 |
| Carboxyvinyl polymer | 0.2 |
| Xanthan gum | 0.2 |
| Preservative | trace amount |
| Fragrance | trace amount |
| Purified water | To 100 |

<2-4> Facial Cleanser (Cleansing Foam)

To produce an antimicrobial facial cleanser (cleansing foam) containing the peptide of the present invention, blending can be carried out as described in the following Table 10 and production can be made according to a common production method in the cosmetic field.

TABLE 10

Facial cleanser composition

| Component | Content (% by weight) |
| --- | --- |
| Peptide of the present invention | 0.1 to 30 |
| Sodium N-acylglutamate | 20.0 |
| Glycerin | 10.0 |
| PEG-400 | 15.0 |
| Propylene glycol | 10.0 |
| POE (15) oleyl alcohol ether | 3.0 |
| Laurin derivatives | 2.0 |
| Methyl paraben | 0.2 |
| EDTA-4Na | 0.03 |
| Fragrance | 0.2 |
| Purified water | To 100 |

<2-5> Nutritive Cream

To produce an antimicrobial nutritive cream containing the peptide of the present invention, as described in the following Table 11, production can be made according to a common production method in the cosmetic field.

TABLE 11

Nutritive cream composition

| Component | Content (% by weight) |
| --- | --- |
| Peptide of the present invention | 0.1 to 30 |
| Vaseline | 7.0 |
| Fluid paraffin | 10.0 |
| Bees wax | 2.0 |
| Polysorbate 60 | 2.5 |
| Sorbitan sesquioleate | 1.5 |
| Squalane | 3.0 |
| Propylene glycol | 6.0 |
| Glycerin | 4.0 |
| Triethanolamine | 0.5 |
| Xanthan gum | 0.5 |
| Tocopheryl acetate | 0.1 |
| Fragrance, preservative | trace amount |
| Purified water | To 100 |

<2-6> Massage Cream

To produce an antimicrobial massage cream containing the peptide of the present invention, as described in the following Table 12, production can be made according to a common production method in the cosmetic field.

TABLE 12

Massage cream composition

| Component | Content (% by weight) |
| --- | --- |
| Peptide of the present invention | 0.1 to 30 |
| Propylene glycol | 6.0 |
| Glycerin | 4.0 |
| Triethanolamine | 0.5 |
| Bees wax | 2.0 |
| Tocopheryl acetate | 0.1 |
| Polysorbate 60 | 3.0 |
| Sorbitan sesquioleate | 2.5 |
| Cetaryl alcohol | 2.0 |
| Fluid paraffin | 30.0 |
| Xanthan gum | 0.5 |
| Fragrance, preservative | trace amount |
| Purified water | To 100 |

<2-7> Pack

To produce an antimicrobial pack containing the peptide of the present invention, as described in the following Table 13, production can be made according to a common production method in the cosmetic field.

TABLE 13

Pack composition

| Component | Content (% by weight) |
| --- | --- |
| Peptide of the present invention | 0.1 to 30 |
| Propylene glycol | 2.0 |
| Glycerin | 4.0 |
| Polyvinyl alcohol | 10.0 |
| Ethanol | 7.0 |
| PEG-40 (Hydrogenated castor oil) | 0.8 |
| Triethanolamine | 0.3 |
| Fragrance, preservative | trace amount |
| Purified water | To 100 |

The present invention is not limited to Examples and Production examples that are described above and various modifications and changes can be made by a person skilled in the art. Also, an application can be made to cosmetics of various usages including color cosmetics. Furthermore, depending on the effect, use can be made for a pharmaceutical preparation which can be applied to human body by thin coating, i.e., ointment, and it is included in the spirit and scope of the present invention that is defined by the attached claims.

A sequence listing electronically submitted with the present application on Sep. 13, 2021 as an ASCII text file named 20210913_Q59121GR10_TU_SEQ, created on Sep. 1, 2021 and having a size of 5,000 bytes, is incorporated herein by reference in its entirety.

What is claimed is:

1. An antimicrobial peptide having the amino acid sequence of SEQ ID NO: 1 with of the following features:
   the $1^{st}$ and the $20^{th}$ to the $24^{th}$ amino acids are deleted and the $11^{th}$ or the $18^{th}$ amino acid is substituted with lysine (K); or
   the $1^{st}$ and the $20^{th}$ to the $24^{th}$ amino acids are deleted and the $11^{th}$ and the $18^{th}$ amino acids are substituted with lysine (K).

2. The antimicrobial peptide according to claim 1, wherein the antimicrobial peptide has an antimicrobial activity against Gram-positive bacteria, Gram-negative bacteria, yeast, or bacteria having tolerance to antibiotics.

3. The antimicrobial peptide according to claim 2, wherein the Gram-positive bacteria are *Staphylococcus aureus*, *Bacillus subtilis*, or *Listeria monocytogenes*.

4. The antimicrobial peptide according to claim 2, wherein the Gram-negative bacteria are *Escherichia coli*, *Pseudomonas aeruginosa*, or *Salmonella typhimurium*.

5. The antimicrobial peptide according to claim 2, wherein the yeast is *Candida albicans* or *Trichosporon beigelii*.

6. The antimicrobial peptide according to claim 2, wherein the bacteria having tolerance to antibiotics are *Staphylococcus aureus*, *Escherichia coli*, or *Pseudomonas aeruginosa* having tolerance to antibiotics.

7. The antimicrobial peptide according to claim 1, wherein the antimicrobial peptide has low cytotoxicity for cells derived from human.

8. An antibiotic comprising the antimicrobial peptide of claim 1 as an effective component.

9. An antimicrobial cosmetic composition comprising the antimicrobial peptide of claim 1 as an effective component.

10. An antimicrobial food additive comprising the antimicrobial peptide of claim 1 as an effective component.

11. An antimicrobial animal feed additive comprising the antimicrobial peptide of claim 1 as an effective component.

12. An antibiotic biopesticide comprising the antimicrobial peptide of claim 1 as an effective component.

13. An antimicrobial quasi-drug composition comprising the antimicrobial peptide of claim 1 as an effective component.

14. A method for antimicrobial treatment in a subject including administering a pharmaceutically effective amount of the antimicrobial peptide of claim 1 to the subject.

* * * * *